United States Patent
Nagai

(10) Patent No.: US 8,647,119 B1
(45) Date of Patent: Feb. 11, 2014

(54) METHODS AND KITS WITH FLUORESCENT PROBES FOR CARIES DETECTION

(75) Inventor: Shigemi Nagai, Lexington, MA (US)

(73) Assignee: President and Fellows of Harvard College, Cambridge, MA (US)

(*) Notice: Subject to any disclaimer, the term of this patent is extended or adjusted under 35 U.S.C. 154(b) by 285 days.

(21) Appl. No.: 12/729,060

(22) Filed: Mar. 22, 2010

Related U.S. Application Data

(63) Continuation-in-part of application No. 11/787,158, filed on Apr. 13, 2007.

(60) Provisional application No. 60/792,768, filed on Apr. 18, 2006, provisional application No. 60/819,135, filed on Jul. 7, 2006, provisional application No. 60/850,922, filed on Oct. 11, 2006, provisional application No. 60/901,421, filed on Feb. 15, 2007, provisional application No. 61/161,978, filed on Mar. 20, 2009.

(51) Int. Cl.
*A61C 5/00* (2006.01)
*A61C 1/00* (2006.01)
*A61C 3/00* (2006.01)

(52) U.S. Cl.
USPC ............................................. 433/215; 433/29

(58) Field of Classification Search
USPC ............... 433/29–31, 215, 224, 229; 424/9.7, 424/9.71, 9.8, 49–54; 606/88–89; 382/128
See application file for complete search history.

(56) References Cited

U.S. PATENT DOCUMENTS

| | | | | |
|---|---|---|---|---|
| 3,309,274 A | * | 3/1967 | Brilliant | 424/9.6 |
| 3,418,716 A | * | 12/1968 | Woods | 433/149 |
| 4,150,485 A | | 4/1979 | Lee et al. | |
| 4,220,450 A | | 9/1980 | Maggio | |
| 4,277,437 A | | 7/1981 | Maggio | |
| 4,347,233 A | | 8/1982 | Yamauchi et al. | |
| 4,382,784 A | | 5/1983 | Freller | |
| 4,479,499 A | * | 10/1984 | Alfano | 600/477 |
| 4,641,650 A | * | 2/1987 | Mok | 606/12 |
| 5,013,553 A | * | 5/1991 | Southard et al. | 514/279 |
| 5,330,357 A | * | 7/1994 | Keller | 433/215 |
| 5,433,952 A | | 7/1995 | Sipos | |

(Continued)

FOREIGN PATENT DOCUMENTS

| | | |
|---|---|---|
| EP | 2006125650 A1 | 11/2006 |
| WO | 2002083023 A1 | 10/2002 |
| WO | 2005025528 A1 | 3/2005 |
| WO | 2007038683 A2 | 9/2006 |

OTHER PUBLICATIONS

Brown et al. 2000 J Am Dent Assoc 131: 223-231.
Dennison et al. 2005 Dent Clin N Am 49: 825-845.

(Continued)

*Primary Examiner* — Yogesh Patel
(74) *Attorney, Agent, or Firm* — Lawson & Weitzen LLP; Sonia K. Guterman; Teofilo Javier, Jr.

(57) ABSTRACT

Methods and kits are provided for identifying carious lesions using a detectable fluorescent probe that binds to the lesion and an optical device. The detectable probe includes a molecule, a stain, a marker, and a dye capable of binding to a caries in the enamel layer of a tooth. The detectable probe is a fluorescent composition, or a bioluminescent composition, that emits a characteristic wavelength of light following illumination at an excitation wavelength.

34 Claims, 18 Drawing Sheets

(56) References Cited

U.S. PATENT DOCUMENTS

| | | |
|---|---|---|
| 5,759,038 A | 6/1998 | Fischer |
| 5,957,687 A * | 9/1999 | Brilliant .......................... 433/31 |
| 6,024,562 A * | 2/2000 | Hibst et al. ...................... 433/29 |
| 6,076,948 A | 6/2000 | Bukosky et al. |
| 6,102,704 A * | 8/2000 | Eibofner et al. ............. 433/215 |
| 6,186,780 B1 | 2/2001 | Hibst et al. |
| 6,276,934 B1 | 8/2001 | Rakocz |
| 6,325,623 B1 * | 12/2001 | Melnyk et al. .................. 433/29 |
| 6,552,794 B2 | 4/2003 | Garini |
| 6,854,974 B1 | 2/2005 | Suhonen |
| 6,992,180 B1 | 1/2006 | Engelhardt et al. |
| 2002/0093655 A1 | 7/2002 | Everett et al. |
| 2004/0023184 A1 * | 2/2004 | de Josselin et al. ............. 433/30 |
| 2004/0191729 A1 * | 9/2004 | Altshuler et al. ............. 433/215 |
| 2004/0248062 A1 | 12/2004 | Hahn et al. |
| 2005/0003323 A1 * | 1/2005 | Katsuda et al. .................. 433/29 |
| 2005/0058602 A1 | 3/2005 | Ramji et al. |
| 2005/0089820 A1 * | 4/2005 | Allred et al. .................. 433/215 |
| 2005/0118115 A1 | 6/2005 | Fontenot |
| 2005/0176029 A1 | 8/2005 | Heller et al. |
| 2005/0181333 A1 | 8/2005 | Karazivan et al. |
| 2005/0207978 A1 | 9/2005 | Ito et al. |
| 2005/0283058 A1 | 12/2005 | Choo-Smith et al. |
| 2006/0034780 A1 | 2/2006 | Guan et al. |
| 2006/0084036 A1 * | 4/2006 | Boston .......................... 433/215 |
| 2006/0127327 A1 | 6/2006 | Shi et al. |
| 2006/0127861 A1 | 6/2006 | Villoresi et al. |
| 2006/0141422 A1 * | 6/2006 | Philp et al. ................... 433/215 |
| 2006/0223032 A1 * | 10/2006 | Fried et al. ................... 433/215 |
| 2007/0031776 A1 | 2/2007 | Sakaguchi |
| 2007/0184402 A1 * | 8/2007 | Boutoussov et al. ........... 433/29 |
| 2007/0280888 A1 * | 12/2007 | Fujikawa et al. ............ 424/9.71 |
| 2008/0085493 A1 | 4/2008 | Sun et al. |

OTHER PUBLICATIONS

PCT/ISA/210, US, May 19, 2008, Nagai.
Du et al. 1998 Photochem Photobiol 68 (2): 141-142.
Fletcher et al. 2005 Clinical Epidemiology:The Essentials, 4th ed., Lippincott Williams & Wilkins: Baltimore, MD, pp. 35-58.
Gobin et al. 2005 Lasers Surg Med 37: 123-129.
Gottlieb et al. 1987 Anal Biochem 165: 33-37.
Hall et al. 2004 J Dent Res 83: C89-C94.
Hannigan et al. 2000 Caries Res 34: 103-108.
Heinrich-Weitzen et al. 2003 Quintessence Int 34: 181-188.
Kang et al. 1996 Caries Res 30: 156-162.
Kuhnisch et al. 2007 Caries Res 41: 43-48.
Landsman et al. 1976 J Appl Physiol 40 (4): 575-583.
Mazzola 2003 Nature 21(10): 1137-1143.
Mccomb 2000 J Can Dent Assoc 66: 195-198.
Nyvad 2004 Caries Res 38: 192-198.
O'Brien et al. 1989 J Dent Res 68 (2): 157-158.
Schneiderman et al. 1997 Caries Res 31: 103-110.
Shi et al. 2000 Caries Res 34: 151-158.
Stookey 2005 Dent Clin N Amer 49: 753-770.
Vaarkamp et al. 1997 J Dent Res 76 (4): 875-882.
Van De Rijke et al. 1990 J Dent Res 69 (5): 1184-1187.
Walsh 2003 Austr Dent J 48 (3): 146-155.
Walsh et al. 2010 "Fluroide toothpastes of different concentrations for preventing dental caries in children and adolescents" in The Cochrane Library, published Issue 2, 2010.
Wenzel et al. 1990 Caries Res 24: 327-333.
White et al. 1997 Dentomaxillofac Radiol 26: 32-38.
White et al. 2003 Oral Radiology: Principles and Interpretation, 5th ed., Mosby: St. Louis, MO.

* cited by examiner

METHODS AND KITS WITH FLUORESCENT PROBES FOR CARIES DETECTION

RELATED APPLICATIONS

This application claims the benefit of provisional application Ser. No. 61/161,978 filed Mar. 20, 2009 in the U.S. Patent and Trademark Office, and is a continuation-in-part and claims the benefit of utility application Ser. No. 11/787,158 filed Apr. 13, 2007, which claims the benefit of provisional application Ser. Nos. 60/792,768, 60/819,135, 60/850,922, and 60/901,421 filed Apr. 18, 2006, Jul. 7, 2006, Oct. 11, 2006 and Feb. 15, 2007, respectively, in the U.S. Patent and Trademark Office, each of which is hereby incorporated by reference herein in its entirety.

TECHNICAL FIELD

Methods, kits and compositions are provided for detecting caries at an early stage using compounds that bind preferentially to the caries, and pre-carious lesions are detected by absorption, luminescence, or by fluorescence.

BACKGROUND

Caries and periodontal disease remain the main reasons for tooth loss worldwide, despite positive effects of preventive measures to reduce caries primarily through the application of fluoride. If detected early before demineralization of the tooth surface has reached the dentin, an incipient caries lesion can be cured by remineralization.

If however the lesion has progressed into the dentin, restorative procedures such as placing amalgam or composite fillings into the treated caries become necessary. Such restorative procedures are in general more invasive and represent a much greater expense to a patient or a third party provider than preventive or curative procedures. Thus, early detection of carious lesions is a key element in the prevention and treatment of dental caries.

Indices and methods of conducting surveys for the level of dental disease were developed between 1900 and 1950. Modern epidemiological studies began after that, and many reliable studies have been conducted since 1960. Concluding remarks of the Symposium of the ORCA Caries Diagnosis Working Group state that the development of methods for determining whether a carious lesion is stable or progressing is a priority in caries research.

The poor diagnostic performance of conventional caries detection methods has prompted the research community to develop quantitative detection methods, such as electrical conductance measurements, light scattering methods, and laser fluorescence methods, in addition to the X-ray technique which is the current standard. Motivations for this development include that quantitative methods detect lesions at an earlier stage than conventional methods, are more reliable than qualitative measurements, and provide methods for monitoring the course of disease in a way that is non-detrimental to the patient.

A systematic review of diagnostic methods prepared for the 2001 National Institutes of Health Consensus Development Conference on 'Diagnosis and Management of Dental Caries through Life' was unable to establish relative efficacies of various methods currently used to detect dental caries. New methods and criteria are needed for diagnosis and prognosis of caries and periodontal disease.

SUMMARY

An aspect of the invention provides a method for detecting an early stage dental caries in a subject, the method including: contacting a caries lesion which is at an early stage, by selective binding of an optically detectable probe to the caries, such that the probe is a composition capable of binding the caries; and, detecting the caries having bound probe using an optical device.

A related embodiment of the method provides detecting the bound probe by contacting a tooth with a fluorescent probe, which is at least one of: a tetracycline, a HiLyte Fluor, an OsteoSense 750, a Cy7, a Qdot, a CardioGreen (ICG), an IR820 (ICG), a Far-Green Two, an AngioSense 750, a Genhance 750, an AngioSpark 750, an Alexa Fluor 750, an Indocyanine Green, a Doxorubicin, a Riboflavin, a Chlorophyll A, a bacterial Chlorophyll and a Porphyrin; and illuminating the tooth at an excitation wavelength, such that diagnosing includes detecting an area of light emission at an emission wavelength. In general, the early stage caries is prior to cavitation or advanced demineralization. In a related embodiment, detecting the caries is observing an area by photometry.

A related embodiment of the method provides the probe which is tetracycline, and detecting the caries with selectively bound tetracycline probe is observing a white spot. For example, the tetracycline fluorescence probe includes at least one of chlorotetracycline, oxytetracycline, and doxycycline.

In general, the caries is detected as a gray, silver, white, brown, yellow or translucent spot diagnosed on the surface of enamel, and the distance of the caries to the surface is in a range of about 10 micrometers (microns; $\mu m$) to about 100 micrometers, about 10 micrometers to about 500 micrometers, about 50 micrometers to about 100 micrometers, about 50 micrometers to about 500 micrometers, about 100 micrometers to about 500 micrometers, or a combination thereof. For example, the early stage caries is located within about one-half a depth of the enamel.

The caries in an embodiment of the method is interproximal. A related embodiment of the method further provides, prior to contacting: accessing an interproximal region by inserting a spacer; and delivering the probe into the interproximal area using at least one device selected from: spray, a wedge, a tape, a metal strip, a plastic strip, a sponge, a syringe, a brush, a string, a tip, and a tray.

In general, the duration of contacting is at least about 10 seconds, for example, at least about 20 seconds, at least about 40 seconds, or at least about 60 seconds.

In general, an area having a gray, silver, white, brown, yellow, or translucent spot is an indication of a location of the caries. The size of an area having a gray, silver, white, brown, yellow, or translucent spot is an indication of an extent of the caries.

The optical device in embodiments of the method is a hand-held intra-oral optical device for illuminating and/or detecting. For example, the tooth is illuminated and the fluorescence is detected using at least one device selected from: a near-infrared (NIR) lamp, light emitting diode (LED) lamp, an ultra-violet lamp or a hand-held intra-oral device attachment connected to a detector selected from the group of: a charge-coupled device (CCD) camera, an optical camera, and a spectrophotometer.

An embodiment of the method further includes detecting fluorescence by placing a separator between teeth. For example, the separator is black or gray, and the separator reduces fluorescence from an adjacent tooth. An embodiment of the method further includes prior to contacting, detecting a presence of an autofluorescence. For example, detecting a presence of an autofluorescence includes detecting autofluorescence of enamel and/or dentin.

An embodiment of the method further includes removing the probe bound to a tooth, for example, removing the probe includes delivering a fluid with a syringe. The fluid is a solution having at least one solute selected from: hydrogen peroxide, phosphoric acid, sodium phosphate monobasic, sodium phosphate dibasic, methylene phosphoric acid sodium chloride, potassium chloride, pyrophosphate dibasic, and pyrophosphate tetrabasic. Alternatively, removing the probe includes delivering a composition, for example a paste or gel. Further, removing the probe includes at least one device selected from: spray, a wedge, a tape, a metal strip, a plastic strip, a sponge, a brush, a string, a tip, and a tray.

An embodiment of the method further provides curing the detected caries by remineralizing. For example, remineralizing includes applying calcium phosphate to the tooth of the subject. In general, the subject is a mammal. For example, the subject is a human.

A related embodiment of the method of remineralizing further provides monitoring the caries lesion, and observing that further caries development is prevented or reduced.

An embodiment of the method further includes preparing a photographic image of an area of the caries with bound probe and comparing the image to a fluorescent image of the probe bound to caries, such that comparing is analyzing at least one selected from the group of: identity, size and depth of the caries lesion.

In an embodiment of the method in which the fluorescent probe is an OsteoSense 750, the method further includes illuminating at an excitation wavelength of about 740 nm to about 760 nm, and diagnosing by detecting emission of fluorescence at a wavelength of about 770 nm to about 790 nm.

Other embodiments provide the fluorescent probe selected from: a tetracycline, a HiLyte Fluor, an OsteoSense 750, a Cy7, a Qdot, a CardioGreen (ICG), an 18820 (ICG), a Far-Green Two, an AngioSense 750, a Genhance 750, an AngioSpark 750, an Alexa Fluor 750, an Indocyanine Green, a Doxorubicin, a Riboflavin, a Chlorophyll A, a bacterial Chlorophyll, a Porphyrin, and a combination thereof; and the method further includes illuminating the tooth at the excitation wavelength selected from: about 350 nm to about 450 nm, about 400 nm to about 500 nm, about 400 nm to about 750 nm, about 550 nm to about 650 nm, about 600 nm to about 650 nm, about 700 nm to about 770 nm, about 710 nm to about 730 nm, about 720 nm to about 750 nm, about 740 nm to about 760 nm, about 750 nm to about 800 nm, or illuminating the tooth at an excitation wavelength of about 775 nm; and detecting light emission selected from: about 450 nm to about 600 nm, about 500 nm to about 700 nm, about 600 nm to about 700 nm, about 650 nm to about 750 nm, about 670 nm to about 900 nm, about 750 nm to about 800 nm, about 750 nm to about 900 nm, about 760 nm to about 780 nm, about 760 nm to about 800 nm, about 770 nm to about 780 nm, about 770 nm to about 790 nm, about 775 nm to about 825 nm, about 820 nm to about 870 nm, or detecting the light at an emission wavelength of about 845 nm.

In an embodiment of the method, illuminating the tooth involves illuminating an entire tooth surface. Alternatively, illuminating the tooth involves illuminating a portion or part of a tooth surface In general, illuminating includes scanning the surface with a beam of illuminating light. The beam forms an angle relative to orientation of enamel prism. For example, the angle is parallel to the orientation of the enamel prism, or the angle is perpendicular to the orientation of the enamel prism, or the angle is acute to a plane of the enamel prism.

In related embodiments, illuminating the tooth involves directing light through an occlusal layer of enamel. Alternatively, illuminating the tooth involves directing light to an interproximal area or adjacent to an interproximal area.

BRIEF DESCRIPTION OF THE DRAWINGS

FIG. 11 panel A shows fluorescence from zero (0) minutes to 30 minutes for Cy7 diluted 1:10 and bound to caries on a demineralized enamel surface.

FIG. 11 panel B and FIG. 11 panel C show fluorescence from 0 minutes to 20 minutes for OsteoSense 750 diluted 1:100 and diluted 1:10, respectively, and bound to caries on a demineralized enamel surfaces.

FIG. 11 panel D shows fluorescence from 0 minutes to 15 minutes for 18820 diluted 1:10 and bound to caries on a demineralized enamel surface.

FIG. 16 panel A shows a tooth with no caries lesion. FIG. 16 panel B shows a tooth with a caries lesion that extends less than one-half of the depth of the enamel (FIG. 16 panel B, left), and a tooth with a caries lesion that extends more than one-half of the depth of the enamel (FIG. 16 panel B, right).

DETAILED DESCRIPTION

Detecting early interproximal lesions still poses a challenge in clinical dentistry today. Invasive restorative treatment is often necessary by the time carious lesions are detectable by bitewing radiographs as shown in Brown L. J. et al., 2000 J Am Dent Assoc 131(2): 223-31, and Hannigan A. et al., 2000 Caries Res 34: 103-108. Therefore, a more sensitive method for detecting early interproximal lesions would provide an opportunity for active preventive measures. Although there are many parallel efforts to detect early caries, devices fail to detect incipient interproximal lesions reliably (Hall A. et al., 2004 J Dent Res 83 (Spec Iss C): C89-C94; Heinrich-Weltzien R. et al., 2003 Quintessence Int 34(3): 181-188; and Stookey G. K., 2005 Dent Clin North Am. 49(4): 753-770).

While the current industry-accepted standard for caries detection is a combination of clinical and radiographic examination, the intra-oral optical device has potential to detect a very small optical property change which are missed by the human eye. Such a development would spare patients from exposure to the radiation associated with radiographs, could reduce labor-intensive clinician time in detecting very early stage caries, and make detection possible for caries that might otherwise go undetected until a later stage.

Figure 1A:
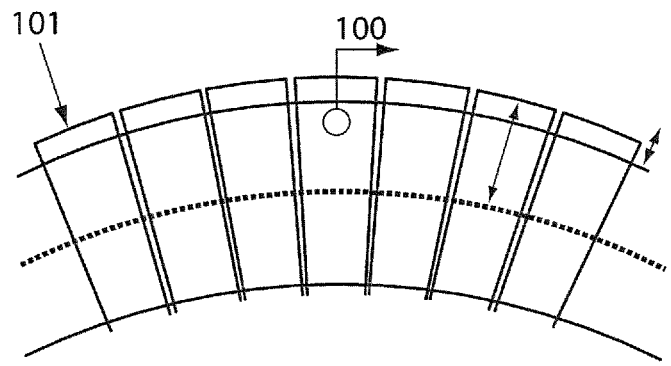
FIG. 1 is a set of drawings showing the development/nature of a "white spot" (100) lesion, an early stage dental caries, that generally is formed by acid and bacteria invading the area between adjacent enamel prisms. An enamel prism (101) is a crystallized hydroxyapatite (HA) rod radiating from the underlying dentin. Enamel prism at a depth of about 100 micrometers or microns (μm) has a very strong and transparent layer. The white spot appears as a white area and shines through the enamel prism. A white spot forms within about 10 μm to about 100 μm, or within about 10 μm to about 150 μm of the surface of the enamel, or within one-half of the depth of enamel. The dotted line indicates one-half depth of the enamel prism. Early stage dental caries are not detected by traditional X-rays because X-ray detection requires that the lesion be larger than about one-half the depth of the enamel. A caries (102) that has extended beyond about one-half the enamel depth is visible and detected by X-rays.
Figure 1B:
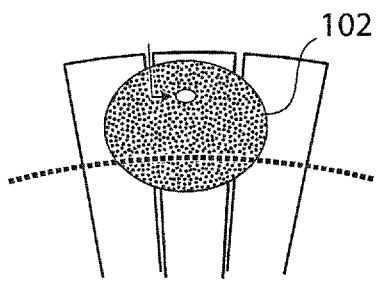

Demineralization on an enamel surface of a tooth results from the presence in the oral cavity of acid and bacteria, and these agents initiate dental caries. FIG. 1 shows that interaction/invasion of acid/bacteria into tooth enamel (i.e., enamel prism) produces a white spot (100) caries lesion that is not detected using conventional X-rays. Hence a molecule capable of binding as a positive/negative ion or by electrovalent bonds in the region of an early stage caries, i.e., an area of demineralization, is here envisioned without limitation as a potential probe for binding to early stage caries.

Examples herein show classes of useful probes that have detectable properties with respect to light: probes that fluoresce in excitation light illumination; probes that generate fluorescence without excitation by light, viz., bioluminescent probes such as the system of luciferase and luciferin; and probes that absorb illuminating light such as Bismuth, Gold colloid.

A slight difference of at least one of the standard optical properties (pattern of reflectance curves, color readings, Scattering/Absorption coefficients, or any other optical data) was sought herein in order to distinguish a caries lesion, from a sound tooth structure, and a handheld unit is programmed such that it is designed to take accurate optical properties of caries lesions in patients' oral cavities. Surprisingly, these differences were detected experimentally using the classes of probes described in examples herein. Therefore, using an optical device to detect potential changes in early lesions, such as an extent of binding of a probe capable of fluorescence or biofluorescence using another class of agent, is described herein as a tool for detecting early stage caries.

The wavelength of illumination (excitation) and emission for fluorescence probes were optimized for each probe. For example the excitation and emission fluorescence for HiLyte Fluor is about 720 nm to about 750 nm and is about 750 nm to about 800 nm, respectively. Data for additional probes are readily determined without undue experimentation according to the methods shown in the present application.

A standard optical device is modified for suitable use in the methods and compositions provided in the present application. Illuminating light was used on an entire tooth surface, for example, by scanning the surface with the beam of illuminating light. Scanning was particularly important for detection of presence of a caries lesion in an interproximal area. Further the examples herein show that angle of illumination was also important, such that illumination in an orientation parallel to or perpendicular to the direction of the enamel prism was particularly effective in detection of probe. In addition, examples herein showed that illumination directly through the occlusal layer of the enamel or to an interproximal area or adjacent to an interproximal area was also effective. Thus, the present invention provides methods for detecting an early stage dental caries in a subject involving contacting a tooth to determine presence of a caries lesion, selective binding of an optically detectable probe to the caries; such that the probe includes a composition or molecule capable of binding the caries; and detecting the caries having bound probe using an optical device. It will be appreciated that the methods shown in the present application involved illuminating the tooth surface by a number of methods shown herein.

Among the optical device used with the various probes, detection was well obtained using a camera, for example, a small camera such as a fiber optic camera. Additional criteria with respect to the optical device was the size of diameter of beam of illuminating light that directly contacted the tooth (a smaller beam generated superior data); diameter of camera for detection of probes that absorbed light (a smaller diameter was superior, similarly to considerations of use of an endoscope); diameter of camera for detection of probes that were fluorescent (smaller was superior, similarly to considerations involved in use of an endoscope); and, illumination for scanning and a camera capable of recording light emissions in the scanning light.

Studies of caries detection indicated a lack of precise optical methods to detect an interproximal caries lesion. Although detection based on near infrared (NIR) was found to capture images of an interproximal lesion, a substantial number of false positive hits were found, and therefore this approach remains far from clinical use. However, compositions are shown in examples herein that bind specifically to caries and are detected using an optical device.

The phrase, a "white spot" (100) as used herein refers to a very early stage of decay that starts within enamel, for example within about 100 µm to 150 µm or less of the surface of the enamel. See FIG. 1. White spot (100) as used herein refers to a stage and size of an early caries lesion. This caries under different conditions is visualized as gray, silver, white, brown, yellow or even translucent.

Bacteria and acid penetrate through the space between (10 µm) enamel prism (101). Demineralization initiated in these areas proceeds towards the surface of enamel. In general, X-ray imaging identifies only a caries lesion (102) having a depth of more than one-half of the enamel layer, so a white spot as defined herein is not detected by X-rays. Further, X-rays have an additional limitation of showing only about 60-70% of the actual extent of a caries. It is envisioned herein that detection of a white spot at an early stage of a lesion, using the methods and techniques herein provides subsequent possibilities for remineralization, and hence a cure for early stage caries. These treatments have potential to substantially improve dental health and lead to reduction of costs.

As used herein, the word "probe" refers to a detectable compound that specifically or preferentially binds a caries lesion. The term includes without limitation a molecule, a stain, a marker, and a dye capable of binding to a caries in the enamel layer of a tooth. In certain embodiments, the probe is a fluorescent composition, for example, tetracycline, HiLyte Fluor, Qdot, OsteoSense 750, Cy7, CardioGreen (ICG), IR820 (ICG), Far-Green two, AngioSense 750, Genhance 750, AngioSpark, 750, Alexa Fluor 750, Indocyanine Green, Doxorubicin, Riboflavin, Chlorophyll A, bacterial Chlorophyll and Porphyrin.

In general the fluorescent compound bound to enamel is detected by illuminating the treated tooth at an excitation wavelength, and detecting an area of light emission at an emission wavelength. In an alternative embodiment, the probe is a bioluminescent compound, for example, using luciferase to detect the compound luciferin or aequorin.

Alternatively, the probe is a composition that absorbs light, for example, bismuth, or colloidal gold. In general, light absorbent compositions are detected by illuminating an area of interest, for example, a tooth with a caries lesion, and detecting an area or region of the tooth that absorbs a specific wavelength of light, such as, absorbance of near infra red (NIR) light.

Gold nanoparticles have been designed that strongly absorb light in the NIR as shown in Gobin et al., Lasers in Surgery and Medicine 37: 123-129 (2005). The gold nanoparticles were used with NIR to provide solder welds in wound-healing research, known as laser-tissue welding and laser-tissue soldering, in a rat skin wound-healing model. Various roles for gold nanoparticles are described by Mazzola, L. in 2003 Nature Biotechnology 21(10): 1137-1143, including molecular detection assays, localized payload delivery, tissue ablation triggered by a secondary mechanism such as light activation, and separation.

The gold nanoshell synthesis in Gobin et al. uses basic reduction of tetraethyl orthosilicate, followed by reaction of the silica core nanoparticles with (3-aminopropyl) triethoxysilane (APTES, Sigma-Aldrich, St. Louis, Mo.), and amine groups on the surface of the core allow for deposition of gold colloid. Gold particles (Auroshell™) are commercially available from Nanospectra Biosciences, Inc. (Houston, Tex.), and from Purest Colloids (MesoGold®, Westampton, N.J.).

Examples herein use Colloidal Gold Total Protein Stain (Bio-Rad, Hercules, Calif.), however it is envisioned that any commercially available colloidal gold preparation would function similarly in detection of early-stage caries.

Tetracycline in addition to its well-known importance as an antibiotic, is a fluorescence incident agent for photometry, for example, for labeling for bone development/formation. Tetracycline however produces tooth discoloration, referred to as "tetracycline teeth" in dentistry. Tetracycline binds to newly formed bone or tooth at the interface and the resultant binding is observed as a line or dot of fluorescence. The phrase, "tetracycline fluorescence" as an agent that binds to newly formed bone or teeth, is capable of fluorescence when illuminated at a pre-determined wavelength of light, and includes, without limitation, all of the members of the tetracycline family as well as additional compositions such as the gold compounds, quantum dot compounds, HiLyte Fluor 750 hydrazide compounds, and any other compounds that share the functional attributes of binding to newly formed bone or teeth and emitting fluorescence or other optical or physical signal upon illumination at a stimulating wavelength.

OsteoSense 750 is a bisphosphonate-conjugated imaging agent used to detect osteogenic activity. OsteoSense 750 acts by targeting hydroxyapatite exposed during times of bone turnover binding thereto with high affinity, thus allowing for in vivo detection and monitoring of skeletal changes. OsteoSense 750 is a commercially available (VisEn Medical, Woburn, Mass.) fluorescent agent that emits light at a wavelength of about 750 nm.

Cy7, or cyanine dye 7, is a fluorescent dye that upon excitation emits light of about 750 nm wavelength. Modified versions of Cy7 are commonly used as fluorescent labels for proteins and antibodies. Cy7 is commercially available from Amersham Biosciences (Piscataway, N.J.). CardioGreen (ICG) is a tricarbocyanine dye that upon excitation emits light of about 800 nm. CardioGreen (ICG) is commercially available from Sigma-Aldrich (St. Louis, Mo.).

IR820 (ICG) is a near-infrared indocyanine dye that upon excitation emits light of about 845 nm. IR820 (ICG) is commercially available from Sigma-Aldrich (St. Louis, Mo.). Far-Green Two is a commercially available dye that that upon excitation, emits light of about in the NIR range. AngioSense 750 is a fluorescence agent that remains localized in vasculature for extended periods of time (approximate half life in plasma 6 h), a property that facilitates imaging, for example, to monitor angiogenesis. AngioSense 750 is commercially available (VisEn Medical, Woburn, Mass.) and emits light at a wavelength of about 780 nm. Genhance 750 is a fluorescence agent, used in the vascular system to facilitate imaging and to monitor angiogenesis. Genhance 750 is a commercially available (VisEn Medical, Woburn, Mass.) fluorescent agent that emits light at a wavelength of about 780 nm. AngioSpark 750 is a fluorescent dye that emits light at a wavelength of about 750 nm. The dye is a macromolecule that is usually useful as it remains localized in vasculature for extended periods of time (approximate half life in plasma 6 hours). AngioSpark 750 has been used to facilitate imaging to monitor angiogenesis, and is commercially available (VisEn Medical, Woburn, Mass.).

Alexa Fluor 750 is a fluorescent dye that upon excitation emits light of about 750 nm wavelength. Alexa Fluor 750 is commercially available from Invitrogen Corp. (Carlsbad, Calif.). Indocyanine Green (ICG) is a tricarbocyanine dye that upon excitation, emits light at wavelengths of about 800 nm, about 820 nm, about 840 nm or at about 860 nm. ICG is commercially available (from H. W. Sands Corp., Jupiter, Fla.) and has been used in infrared photography, the preparation of Wratten filters, and as a diagnostic aid for blood volume determination, cardiac output, or hepatic function. The properties of ICG are described in Landsman et al. 1976 J. Appl. Physiol., 40: 575-583.

Doxorubicin (also known as adriamycin or hydroxyldaunorubicin) is a DNA-interacting cancer drug widely used in chemotherapy. A chemotherapeutic dose of Doxorubicin is in a range of about 60 mg/m$^2$ to 75 mg/m$^2$. Doxorubicin is fluorescent and emits light at wavelengths of about 550 nm, 600 nm, or 650 nm and this property has been used in cell biology research for measurement of drug efflux pump activities and intracellular localization of various multi-drug resistance proteins, at much lower concentrations than the chemotherapeutic dose. Doxorubicin is commercially available from Sigma-Aldrich (St. Louis, Mo.).

Riboflavin (vitamin B$_2$) is an easily absorbed micronutrient with a role in a wide variety of cellular processes, for example, energy metabolism. Riboflavin is an easily absorbed, water-soluble micronutrient that supports energy production by aiding in the metabolism of fats, carbohydrates, and proteins. Riboflavin is also needed for red blood cell formation and respiration, antibody production, and for regulating human growth and reproduction. Riboflavin functions as an antioxidant by scavenging damaging particles in the body known as free radicals, and is important for healthy skin, nails, hair growth and general good health, including regulating thyroid activity. As Riboflavin is water soluble, an excess is not stored and is excreted generally in the urine. As a result, Riboflavin has no known toxic dose. The minimum daily recommended dose ranges from 1 mg to 2 mg as a dietary supplement, while a typical therapeutic daily dose ranges from 50 mg to 100 mg. Substantially less Riboflavin is needed in the methods herein for contacting a surface of a tooth. Riboflavin is commercially available from Sigma-Aldrich (St. Louis, Mo.) and is fluorescent, emitting light at a wavelength of, for example, about 450 nm, about 550 nm, about 650 nm, or about 750 nm. The properties of Riboflavin are described in Du et al. 1998 Photochemistry and Photobiology, 68: 141-142.

Chlorophyll A is a green photosynthetic pigment that emits light at a wavelength of, for example, about 600 nm, about 700 nm, or about 800 nm. Chlorophyll A is commercially available from suppliers such as Sigma Chemical (St. Louis, Mo.) and Turner Designs (Sunnyvale, Calif.). As Chlorophyll A is a normal part of a regular human diet, it has no known toxicity.

Bacterial Chlorophylls or bacteriochlorophylls are photosynthetic pigments that occur in various phototrophic bacteria and do not produce oxygen. Bacterial chlorophylls differ structurally from the chlorophylls of higher plants and from each other structurally. Each bacteriochlorophyll absorbs light energy in a different portion of the spectrum. Examples of bacteriochlorophylls are: bacteriochlorophyll a, bacteriochlorophyll b, bacteriochlorophyll c, bacteriochlorophyll d, bacteriochlorophyll e, and bacteriochlorophyll g. Bacteriochlorophyll a and bacteriochlorophyll b are the photosynthetic pigments of purple bacteria. Bacterial Chlorophylls are fluorescent pigments and emit light at a wavelength, for example, about 350 nm, about 450 nm, about 650 nmm or about 750 nm. Bacterial Chlorophylls are available commercially from Sigma-Aldrich (St. Louis, Mo.).

Porphyrin is a heterocyclic macrocycle made from 4 pyrrole subunits linked on opposite sides through 4 methine bridges (=CH—). The extensive conjugated structure of Porphyin makes the compound chromatic, i.e., fluorescent at a wavelength of, for example, about 600 nm, or about 650 nm, or about 700 nm. Porphyrin is commercially available from Sigma-Aldrich (St. Louis, Mo.). Porphyrin is associated with hemoglobin and myoglobin, which are components of an animal based diet, and is therefore a normal part of a regular human diet, thus it also has no known toxicity.

For bioluminescent probes, excitation energy is supplied by a chemical reaction rather than from an incoming source of light. Luciferin and luciferase are an example of a substrate and its associated enzyme, which catalyzes a light-producing reaction, i.e. bioluminescence, and adenosine triphosphate (ATP) is involved in this reaction. Light is emitted (for example at about 500 nm, at about 550 nm, or at about 650 nm) when luciferase is exposed to the appropriate luciferin substrate in the presence of ATP, and photon emission is detected by a light sensitive apparatus such as the optical devices described herein. Luciferase and luciferin have been widely used, for example, to observe biological processes and stages of infection, and are commercially available from Sigma-Aldrich (St. Louis, Mo.).

Further examples of bioluminescent compositions are green fluorescent protein (GFP) and aequorin. These are bioluminescent compositions are isolated from the jellyfish *Aequorea victoria*. When a calcium ion binds to aequorin, the complex breaks down into apoaequorin and a luminescent composition, which emits blue light (at about 466 nm). Synthetic aequorin is commercially available from Sealite Sciences (Bogart, Ga.) as AQUALITE®. GFP emits light in the lower green portion of the visible spectrum (at about 490 nm to about 570 nm). Synthetic GFP is commercially available from Clontech (Mountain View, Calif.).

The composition known as "quantum dot" consists of a solution of nanometer-scale (roughly protein-sized) atom clusters, exemplified by Qdot® available commercially from Invitrogen (Carlsbad, Calif.). The clusters contain combinations of materials, such as a combination of alkali metals (Li, Na, K, Rd, Cs and Fr), alkaline earth metals (Be, Mg, Ca, Sr, Ba and Ra), transition metals (Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au and Hg), lanthanides (La, Ce, Pr, Nd, Pm, Sm, Eu, Gd, Tb, Dy, Ho, Er, Tm, Yb and Lu) and actinoids (Ac, Th, Pa, U, Np, Pu, Am, Cm, Bk, Cf, Es, Fm, Md, No and Lr) on a silica- or silicone-based core.

Quantum dot preparations have been developed for use as fluors by binding to samples followed by illuminating with light in the UV spectrum. The quantum dot preparations exhibit large molar extinction coefficients, high photostability and strong and size-dependent tunable emission. The tunable aspect of the emission peak is adjusted to be infrared, far-red and red light that accordingly binds to dental enamel by virtue of the commercially available preparations having different combinations of metals and different sizes of particles. In addition, dot particle preparations are available with an overall negative charge or a positive charge, depending on the combination of metals.

Examples herein show that a quantum dot preparation selectively binds to decalcified enamel but not healthy electronically neutral enamel, due to the electronic charge. Furthermore, a quantum dot preparation is conjugated to any of the small compounds described herein, such as tetracycline, calcein, a fluorescent stain used to label intact and living cells (Invitrogen), and their derivatives that have an affinity to decalcified enamel. These conjugates form an "enamel affinity quantum dot" preparation. Decalcified enamel is then detected using the enamel affinity quantum dot as enamel-translucent fluorescence. Alternatively, quantum dots that bind to decalcified enamel are detected by dichroism, such as fluorescence detected circular dichroism.

Yet another example of a useful composition is HiLyte Fluor 750 hydrazide, which is a commercially available fluorescence dye that is used as a detection agent for colloidal gold (AnaSpec, Inc., San Jose, Calif.). HiLyte Fluor 750 hydrazide is a carbonyl-reactive fluorescent labeling dye. It is used for labeling glycoprotein such as horseradish peroxidase (HRP). HiLyte Fluor 750 hydrazide is the longest wavelength carbonyl-reactive HiLyte Fluor dye currently available. Its fluorescence emission is at about 782 nm, well separated from commonly used far-red fluorophores such as HiLyte Fluor 647, HiLyte 680 or allophycocyanin (APC), facilitating multicolor analysis.

The probes herein are suitable for contacting or applying to a mammalian tooth (humans and high value animals) for the detection of an early stage caries lesion to which the probes herein bind, including an amount of a probe of the present methods or a pharmaceutically acceptable salt thereof, which is effective for this detection. The probes according to the methods are those for oral contact or application to a mammalian tooth (humans and high value mammals) that include an effective dose of the probe, alone or together with a significant amount of a pharmaceutically acceptable carrier or buffer. As used herein, the term "pharmaceutically acceptable carrier or buffer" includes any and all solvents, diluents, or other agents, compositions or fluids suited to the effective use of the probe.

The amount of probe used by the dentist is chosen by the individual dentist in view of the patient to be treated. Dosage and administration are adjusted to provide sufficient levels of probe to detect caries. Additional factors which are taken into account include the severity of the caries disease state, e.g., extent of the condition, history of the condition. For example, the desired dosage of the probe depends on the species of the mammal, the body weight, the age and the individual condition, individual pharmacokinetic data, and the mode of administration.

A concentration of a solution of the probe of the present methods or a pharmaceutically acceptable salt thereof to be contacted to a tooth surface, for example an adult human tooth surface, is for example, from approximately 1 ng/ml to approximately 100 ng/ml, from approximately 100 ng/ml to approximately 500 ng/ml, from approximately 500 ng/ml to about 1 µg/ml, from approximately 1 µg/ml to approximately 50 µg/ml, and from approximately 50 µg/ml to approximately 500 µg/ml. Predictive dental doses for children are potentially significantly lower, for example one-half to one-tenth of a concentration suitable for an adult.

A longstanding need in dental medicine is a method for detecting an early stage caries lesion. Compositions herein have not previously been considered as probes for detection of a carious lesion, for example, at a stage associated with initial events such as early demineralization. Another longstanding need is detection of an interproximal lesion, i.e., a lesion located on a surface between teeth. Detecting interproximal lesions at an early stage, i.e., located within one-half of the depth of enamel, using for example bite wing X-rays or by visual clinical inspection, has not previously been possible.

An optical device suitable for detecting the caries with bound probes using to the methods herein includes optical components similar to those found in endoscopes. These optical components include either a rigid or flexible tube containing one or more optical fiber systems, the tube having a channel for mechanical devices, such as a light delivery system used, for example, to illuminate an object under inspection, in the case herein, a surface of a tooth. In certain embodiments, the optical device further includes a device that emits electromagnetic wavelength radiation. Such a device is described in Bukosky et al. (U.S. Pat. No. 6,076,948, issued Jun. 20, 2000).

In one embodiment, the light delivery system includes a light source located outside the oral cavity, with the light directed onto the tooth via an optical fiber system. Alternatively, the optical device contains a built-in light source, such as an LED. In certain embodiments, the optical device includes a lens system to transmit images to the user. The user is able to control the wavelength of the transmitted source, for example, by transmitting light suitable for excitation of a fluorescent probe, a composition that binds to the caries. An example of a hand-held intra-oral light wave detection device is the SharpVision ZE-411 oral endoscope (Sharp Vision Co. Ltd., Guangdong, China).

In certain embodiments, the optical device is an ultra-violet (UV) lamp. UV refers to electromagnetic radiation with wavelengths in the range of about 10 nm to about 400 nm. The UV wavelengths from about 345 nm to about 400 nm produce a "blacklight" effect, i.e., this range of wavelengths causes certain compositions to fluoresce. UV lamps are commercially available from Unilam Co, LTD. (South Korea).

In other embodiments, the optical device is a spectrophotometer. As used here, a spectrophotometer refers to a device for measuring light intensity, i.e., the device measures intensity as a function of the color, or more specifically, the wavelength of light. In certain embodiments, the spectrophotometer is used to detect the fluorescent probe bound to an early caries lesion in a tooth. Spectrophotometers are commercially available from Hitachi Ltd. (San Jose, Calif.). In a related embodiment, the spectrophotometer is a hand-held spectrophotometer such that a technician measures electromagnetic light waves intra-orally (emission or absorbance) from the probes bound to the early stage caries on a tooth. Hand-held spectrophotometers are commercial available from Konica Minolta (Chiyoda-ku, Tokyo).

A probe in embodiments described herein fluoresces at a wavelength within the spectrum of visible light, and is thus detected using a camera to photograph the tooth having an early stage caries lesion to which the probe is bound. As used herein, a camera refers to a device used to capture images as still photographs or as sequences of moving images, for example a charge coupled device (CCD) camera that converts optical brightness into electrical amplitude signals using a plurality of charge coupled devices, and then reproduce the image of a subject using the electric signals without time restriction. A CCD camera is commercially available, for example, from Texas Instruments (Dallas, Tex.).

An optical fiber such as for use in fiber optics is within the scope of the optical devices herein. The optical fiber includes a glass or plastic fiber that transmits light along its length by total internal reflection. The fiber includes a core surrounded by a cladding layer, in which one or more layers of material of lower refractive index are in contact with a core material of higher refractive index. Optical fibers are used herein as light guides, to illuminate an area or locus of a dental surface, including an interproximal surface between teeth. Optical fibers include a coherent bundle of fibers, often along with lenses.

Fiber optics are used by dentists, for example, in preparing a dental filling by light-polymerization of a composition. The hardening process uses blue light with a wavelength of approximately 450 nm produced from a hand-held light source via a fiber rod or fiber taper to the tooth being treated (SCHOTT North America Inc., Southbridge, Mass.). These devices are readily adaptable to the kits and methods herein.

Optical devices are previously described as "probes" in prior publications, however as used herein that term means a composition that binds a caries.

In general the optical detection device captures at least one or at least two images of the tooth, an image that shows the anatomy of the tooth (enamel, dentin, and enamel-dentin junction) and an image that shows fluorescence of the tooth having a caries lesion and probe bound to the lesion. The image of the anatomy of the tooth is detected using light illumination with a device such as a CCD camera, an optical device, or a spectrophotometer to obtain an image of a caries. This image is superimposed with a fluorescence image of using the superposition of the two images. A clinician accurately determines the size, depth and location of the caries. Software to superimpose images is within the scope of the methods and kits herein.

Using the kits and methods herein a tooth surface is contacted with one or more probe compositions. For example, a thin lamella or matrix is coated with probe, and the matrix is applied to the tooth. The matrix is a thin strip of paper, plastic tape, or another convenient applicator. Alternatively an injection type of syringe having a barrel containing a solution of the probe is used to apply a small volume of the probe as a soak. The interproximal region is made more accessible by pre-treating the area with a wedge to widen the space between two or more teeth.

After probe has been contacted to a tooth or teeth and prior to visualizing with an optical device, the area is rinsed at least once with water and/or an aqueous solution to remove excess probe. After detecting the probe, a device, for example a syringe, is used to apply a fluid to further remove probe from the tooth or teeth. The fluid used to remove the probe is for example hydrogen peroxide, for example Opalescence Boost Teeth Whitening system sold by Ultradent Inc. (South Jordan, Utah) contains 38% hydrogen peroxide. Alternatively, the fluid used to remove the probe is a solution of phosphoric acid, sodium phosphate monobasic, sodium phosphate dibasic, methylene phosphoric acid, sodium chloride, potassium chloride, pyrophosphate dibasic, and pyrophosphate tetrabasic. For example, the fluid used to remove the probe is a one of a phosphoric acid solution at a concentration of 5%, 10%, 20%, 40% by weight, or has a range of concentration of 5%-10%, 5%-20%, 10%-20%, 5%-40%, 10%-40% or 20%-40% phosphoric acid solution by weight, or other solutions herein.

As described in this application, fluid for removing probe from the tooth is generally aqueous, or is an organic solvent and in various embodiments includes one or more buffers to provide a stable pH in presence of acid or alkali or upon dilution, and further includes a cation or ion, for example calcium or chloride. The fluid for removing the probe is applied during a time period, for example 1-15 minutes, to interact with the probe on the tooth. Removing the probe using a fluid rinse follows binding and prior to detecting a pre-carious lesion in one embodiment. Alternatively, the probe bound to the lesion is detected directly.

An example of a dental use of optical fibers includes lighting of handpieces. Dental instruments typically include a light source to illuminate the treatment area. A light guide is built into the instrument handpiece for this purpose (SCHOTT North America Inc., Southbridge, Mass.), and such instruments are adapted to the purposes herein.

Figure 2:
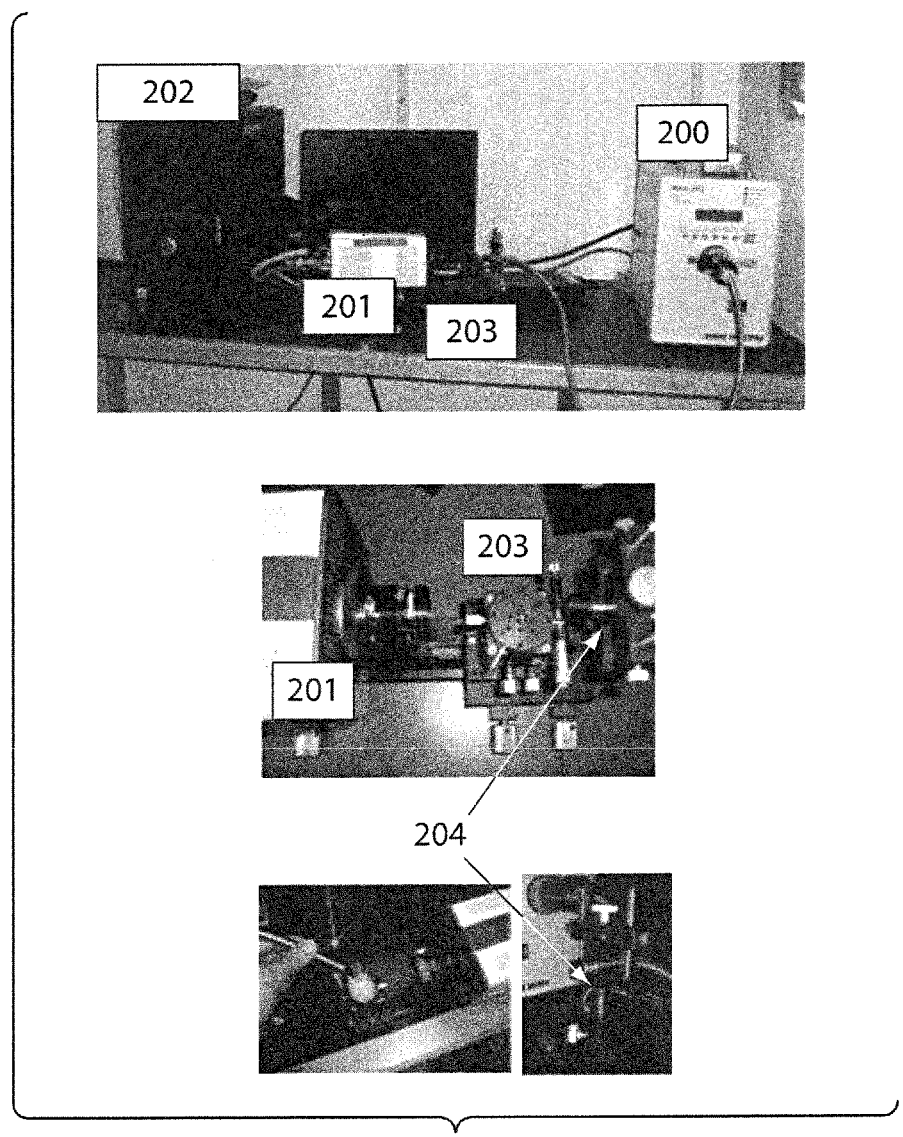
FIG. 2 is a set of photographs showing an optical device system for detecting the probes that are bound to early stage caries lesions in teeth. The photographs show a light source (200) for illuminating a tooth to observe an early stage caries lesion bound to the detectable probe. A camera (201) captures the image of the tooth with an early stage caries lesion and bound probe. A computer (202) coordinates the emitting light source and camera, and further includes data analysis software (e.g., image detection algorithms, sample identification) and stores observed data. A stage (203) holds the sample, i.e., synthetic tooth, bovine tooth, or slice of enamel, having an early stage caries lesion for illumination. An optical fiber (204) transmits and focuses the electromagnetic light waves emitted by light source (200) and directs the waves at an area on the tooth that is on the stage (203).

FIG. 2 shows an optical device system for detecting a probe that is bound to an early stage caries lesion in an experimental tooth or portion thereof. A tooth is placed in stage 203. A light source 200, a MAX301 xenon light (Asahi Spector, China), illuminates an area of the tooth at a wavelength that allows for detection of binding of the probe, i.e., illuminates with light having a wavelength of absorption or emission. In certain embodiments, an optical fiber 204 (Olympus, Melville N.Y.) transmits and focuses the electromagnetic light waves emitted by light source 200 and direct the waves at an area on the tooth that is located on stage 203. The optical fiber 204 is modified to direct the electromagnetic light waves to form a spot illumination, using a silicon cap and paper wrapping. A camera 201, a MC285SPD-L0B0 camera (Texas Instruments, Dallas, Tex.), captures the image of the detectable probe and transmits it to computer 202, Optiplex 20 1 L (Dell Inc., Round Rock, Tex.). A computer 202 uses Capture eBase (Solution Systems, Inc., Rolling Meadows, Ill.), a software program for controlling light source 200, for example, the software controls the wavelength of light source 200, for example, to transmit light suitable for excitation of the probe.

It is envisioned that a dentist will remineralize a tooth determined to have an early stage caries. Remineralization uses compositions and methods that are well-known in the dental arts, for example, a commercially available product, Enamelon, which is a toothpaste having soluble calcium phosphate supplied directly to teeth. Enamelon further contains fluoride, and includes a white toothpaste with calcium and a blue toothpaste with phosphate and fluoride. Squeezing the tube produces side-by-side stripes to produce a remineralizing treatment. Alternatively, one or more of remineralizing gels are applied at a dental visit, for example, treatment about once per month with a topical gel containing 100-150 ppm fluoride, for example, 2.72% acidulated phosphate fluoride, and 2% neutral sodium fluoride. Caution is taken to administer doses that are well below a level of toxicity, and to assure that the subject does not swallow the gel.

Dental caries remain a global chronic disease (Brown L. J., et al. 2000 J Am Dent Assoc 131(2): 223-31). Traditional visual-tactile methods and radiographic methods are generally used to detect caries that are more advanced, for example, advanced caries that are found at a depth of greater than 500 µm of the enamel. These traditional methods fail to diagnose many incipient carious lesions (Stookey G. K., 2005 Dent Clin North Am, 49(4): 753-770). A location such as interproximal prevents these caries from being detected by methods other than by bitewing radiography. However, bitewing radiographs exhibit low accuracy and sensitivity values for detecting interproximal lesions, 65% and 45% respectively (Kang B. O., et al. 1996 Caries Res. 30(2): 156-62; White S. C., et al. 1997 Dentomaxillofac Radiol. January; 26(1): 32-8). Tooth decalcification, about 40% to about 60%, is necessary before lesions are visible in a radiographic image. Thus, incipient lesions are not visible on radiographic images. Further, radiographs have generally been found to underestimate the actual size and/or depth of a carious lesion (Wenzel A., et al. 1990 Caries Res 24(5): 327-33; White S. C., et al. 2003 Oral Radiology: Principles and Interpretation. 5th edition Mosby). By the time an interproximal lesion is visible on a bitewing radiograph invasive class II restorations are required, subjecting the patient's tooth to invasive dental treatments and procedures.

Detection of early caries which are in a reversible state reduces the probability that a subject will need an invasive dental restoration and treatment for caries that generally appear subsequent to these restorations. (Marinho V. C., et al. 2003 Cochrane Database Syst Rev, 1: CD002278). There is a need for an early stage dental caries as an optimal diagnostic tool. Such a system must have good diagnostic performance, be noninvasive, easy to use, and reasonably inexpensive (Kuhnisch J., et al. 2006 Caries Res., 40: 104-111).

Optical tools/devices for caries detection include digital imaging with transillumination (DIFOTI; Schneiderman A., et al. 1997 Caries Res, 31: 103-110), quantitative light-induced fluorescence (QLFI and QLF II; Heinrich-Weltzien R., et al. 2003 Quintessence Int, 34(3): 181-188), and laser fluorescence (DIAGNOdent; Shi X., et al. 2000 Caries Res, 34: 151-158). Optical diagnostic tools that measure changes in light scattering have potential for detecting caries. However, drawbacks affecting suitability include, for example, DIFOTI only operating in the visible light wavelength range, and penetrating insufficiently deeply through enamel. QLF is costly and generally only purchased by universities and research centers (Heinrich-Weltzien R., et al. 2003 Quintessence Int, 34(3): 181-188). DIAGNOdent (Kayo, Biberach/Riss, Germany) detects the Near Infrared (NIR) fluorescence from bacterial porphyrins, however detects only advanced caries that have accumulated a large amount of bacterial byproducts. A study assessing enamel lesions using DIAGNOdent found the combination of the method and device had a sensitivity of only 40% (Shi X., et al. 2000 Caries Res, 34: 151-158). Thus, a device that reliably detects caries, particularly interproximal caries, is needed, to provide consistent and reliable images that accurately represent the size and/or depth of a carious lesion, and promotes an active preventive therapy, for example a system that allows a clinician to make an early diagnosis and to formulate a treatment plan tailored to the individual (Nyvad B., 2004 Caries Res., 38: 192-198).

Wavelengths of light studied for scattering characteristics include scattering probability that decreases with increasing wavelength (Hall A., et al. 2004 J Dent Res, 83(Spec Iss C): C89-C94). A long wavelength of light, 1310 nm, was used to image lesions, discriminate demineralization, staining, and pigmentation, and to investigate developmental defects such as fluorosis. However, this method was not tested in vivo, and an optical device to detect a wavelength of 1310 nm would be extremely expensive.

Early detection of caries permits opportunities for preventive dental measures including minimizing caries from recurring near a restoration, reducing incidence of early restoration failure, decreasing incidence of tooth fracture related to weakened cusps resulting from large restorations, and retaining vitality of dental pulp throughout the lifetime of the subject (Dennison J. B., et al. 2005 Dent Clin N Am, 49: 525-545).

Sensitivity is an important characteristic for detecting a disease that results in negative consequences such as pain, expense and loss of self-esteem. Sensitive tests are especially helpful at the early stages of a diagnostic workup (Fletcher R. H., 2005 Clinical Epidemiology, Chapter 3: Diagnosis, Lippicott). While dental caries do not generally have lethal consequences, progression of this destructive process becomes irreversible and painful and expensive to treat. A sensitive detection method for detecting caries is needed.

Teeth have a number of components and layers including enamel, dentin, cementum, and dental pulp. Enamel varies in thickness across the surface of the tooth and is often thickest at the cusp, up to 2.5 mm, and thinnest at the border, which is seen clinically as the cementoenamel junction. Individual enamel rods measure about 4 µm to about 8 µm in diameter and are the primary component of enamel. An enamel rod, known also as enamel prism (101, FIG. 1 panel A), contains crystalline hydroxyapatite organized in an oriented pattern. These calcified microscopic rods are perpendicular to and radiate from the dentin. The area between individual enamel rods is about 10 µm wide, and is referred to as interrod enamel. Bacteria and acid enter the interrod enamel and result in a white spot (100, FIG. 1 panel A) caries lesion or an incipient caries to form over time.

Examples herein use probes (e.g., fluorescent and bioluminescent) and show that these probes bind to a caries lesion and are detectable. Examples herein show, for example, contacting a fluorescent probe to dental caries, illuminating the tooth with light of an excitation wavelength, and detecting a light signal having at least one emission wavelength. Multiple methods are provided for illuminating the tooth, for example, illuminating the interproximal area directly or illuminating the area through the occlusal layer. Data show that the methods provided herein detected more than 90% of the actual size and/or depth of caries, compared to bitewing X-rays.

It was observed in examples herein that the methods, occlusal illumination and interproximal illumination, resulted in improved sensitivity, specificity, positive predictive value, and negative predictive value results compared to X-rays. The "positive predictive value" is the probability of a true disease state following or in the presence of a positive assessment. The "negative predictive value" is the probability of a false disease state following or in the presence of a false assessment. Examples herein show that the mean negative predictive value of X-rays was about 35%, indicating that the true caries are expected to be found in 65% of negative assessments for this method, i.e., much too high a false negative predictive value. The negative predictive values of occlusal illumination and interproximal illumination observed herein were much greater compared to the negative predictive values obtained for X-ray data. An increased negative predictive value indicates to a dentist that a negative assessment truly indicates the absence of a lesion.

Data obtained in examples herein thus show higher user reliability compared to X-rays. Assessments using each of occlusal illumination images and interproximal illumination images resulted in improved sensitivity compared to X-ray images. Examples herein also showed that assessments using interproximal illumination images resulted in increased sensitivity in detecting early stage caries compared to assessments using occlusal illumination images. It is likely that illuminating through the tooth structure/geometry reduces the amount of light reaching a fluorescent probe. Without being limited by any particular theory or mechanism of action, it is envisioned that other variables affect the observed sensitivity and specificity of the methods described herein, including duration of illumination, distance from the tooth during the period of illuminating, etc.

Enamel and dentin generally autofluoresce at wavelengths of about 500 nm to about 700 nm. Data herein show that fluorescent probes respond to a longer excitation wavelength and minimize an overlapping fluorescence range to minimize effects of autofluorescence. A longer wavelength of light in the NIR range yields less scatter, resulting in greater amounts of light penetrating teeth more completely without compromising the contrast of the obtained image.

An aspect of the invention provides a method for detecting early dental caries in a subject, the method including, contacting a caries lesion at an early stage by selective binding an optically detectable probe to the caries, such that the probe includes a molecule capable of biding the caries, and detecting the caries having bound probe, by using an optical device. The early stage caries is prior to demineralization, i.e., the caries is a "white spot" or an incipient stage of caries. In general, the early stage caries is prior to cavitation or advanced demineralization.

In various embodiments of the method herein, detecting the bound probe further includes a step of contacting a tooth with a fluorescent probe, and the fluorescent probe is at least one selected from the group of tetracycline, Hilyte Fluor, OsteoSense 750, Cy7, Qdot, CardioGreen (ICG), IR820 (ICG), Far-Green Two, AngioSense 750, Genhance 750, AngioSpark 750, Alexa Fluor 750, Indocyanine Green, Doxorubicin, Riboflavin, Chlorophyll A, bacterial Chlorophyll and Porphyrin, the method further includes illuminating the tooth at an excitation wavelength, diagnosing by detecting an area of light emission at an emission wavelength. In an alternative embodiment of the method, detecting the selective binding further includes a step of contacting the tooth with the probe, which is a chemiluminescent substrate such as luminal and luciferin, and the method further includes contacting the tooth with other reactants such as hydrogen peroxide, luciferase, and metal ions as catalysts, and diagnosing is detecting an area of bioluminenesce.

In another embodiment of the method, detecting selective binding further includes a step of contacting the tooth with a colloidal gold, and diagnosing is detecting an area of absorbance of near infra red (NIR) light. Alternatively detecting the selective binding further includes a step of contacting the tooth with a quantum dot composition probe, and diagnosing is detecting fluorescence or fluorescence dichroism. Alternatively, detecting the selective binding further includes a step of contacting a tooth with a probe that is a conjugate of a quantum dot composition, and the conjugate is attached to at least one second agent selected from the group of a tetracycline, bismuth, a colloidal gold or the like, for example, good nanoshell particles, followed by detecting fluorescence or fluorescence-detected dichroism. Alternatively, detecting the selective binding further includes a step of contacting a tooth with colloidal gold, and diagnosing is detecting fluorescence with a HiLyte Fluor 750 hydrazide. In various embodiments, the duration of contacting is at least about 10 seconds, at least about 20 seconds, at least about 40 seconds, or at least about 60 seconds.

In another embodiment of the method, the probe is tetracycline and detecting the caries with selectively bound tetracycline probe is observing a white spot. In general, the caries is a gray, silver, white, brown, yellow or translucent spot diagnosed on the surface of enamel, or within an under layer of about 50 to about 100 micrometers (microns; μm) of the surface, or about 50 μm to about 500 μm of the surface, or about 100 μm to about 500 μm of the surface. In general, an area having a gray, silver, white, brown, yellow or translucent spot is an indication of a location of the caries. In general, the size of an area having a gray, silver, white, brown, yellow or translucent spot is an indication of an extent of the caries. In yet another embodiment of the method, the caries with the selectively bound quantum dot probe is a spot of enamel-translucent fluorescence.

In an embodiment, the caries is interproximal, and the method further involves prior to contacting at least one step of: accessing an interproximal region by inserting a spacer; and delivering the probe into the interproximal area using at least one device selected from the group of: a metal strip, a plastic strip, a sponge, a syringe, a brush, a string, a tip, and a tray. For example, the probe is a solution, a gel, or a mousse. In another embodiment, the conjugate comprises a quantum dot composition or a HiLyte Fluor 750 hydrazide. In another embodiment, the tetracycline fluorescence probe comprises at least one of chlorotetracycline, oxytetracycline, and doxycycline.

In general, the optical device is a hand-held intra-oral optical device. For example, the fluorescence is detected using at least one device selected from the group consisting of a NIR lamp, LED lamp, an ultra-violet lamp and a hand-held intra-oral device attachment connected to at least one detector selected from the group consisting of a charge coupled device (CCD) camera, an optical camera and a spectrophotometer. Alternatively, detecting the caries is observing by photometry or preparing a photographic image of an area of the caries with bound probe and comparing the fluorescent image to determine at least one selected from the group of identity, size, and depth of the caries lesion.

In general, the method further involves detecting fluorescence by placing a separator between teeth. For example, the separator is black or gray and reduces fluorescence from an adjacent tooth.

In general, the method further involves prior to contacting, detecting presence of autofluorescence. In general, the method further involves removing the probe bound to a tooth, for example, by delivering a fluid with a syringe. In an embodiment, the fluid is at least one selected from the group of: a solution, a gel, and a mousse. In one embodiment of the method, the solution is selected from a group consisting of hydrogen peroxide, phosphoric acid, sodium phosphate monobasic, sodium phosphate dibasic, methylene phosphoric acid, sodium chloride, potassium chloride, pyrophosphate dibasic, and pyrophosphate tetrabasic.

In another embodiment of the method, the method further involves curing the detected caries by remineralizing the tooth of the subject, which is a mammal. For example, the subject is a human. In certain embodiments of the method, the method further involves remineralizing the caries lesion, such that the caries lesion is monitored, and is prevented or reduced.

In an embodiment, the optically detectable probe is charged. In general, the probe is a fluorescent probe. For example, the fluorescent probe is a tetracycline, the wavelength for illuminating the tooth is about 350 nm to about 450 nm, and a wavelength for detecting its fluorescence is about 450 nm to about 600 nm. Alternatively, the fluorescent probe is Hilyte Fluor, the wavelength for illuminating the tooth is about. 720 nm to about 750 nm, and a wavelength for detecting its fluorescence is about 750 nm to about 800 nm. Alternatively, fluorescent probe is OsteoSense 750, the wavelength for illuminating the tooth of about 740 nm to about 760 nm, and a wavelength for detecting is fluorescence of about 770 nm to about 790 nm. Alternatively, the fluorescent probe is Cy7, the wavelength for illuminating the tooth is about 700 nm to about 770 nm, and the wavelength for detecting its fluorescence is about 760 nm to about 800 nm. Alternatively, the fluorescence probe is a Qdot, the wavelength for illuminating the tooth is about 400 nm to about 750 nm, and the wavelength for detecting its fluorescence is about 750 nm to about 900 nm.

In yet another embodiment, the fluorescent probe is CardioGreen (ICG), the wavelength for illuminating the tooth is about 750 nm to about 800 nm, and the wavelength for detecting its fluorescence is about 820 nm to about 870 nm. Alternatively, the fluorescent probe is IR820, the wavelength for illuminating the tooth is about 775 nm, and the wavelength for detecting its fluorescence is about 845 nm. Alternatively, the fluorescent probe is Far-Green two, which involves illuminating the tooth at a wavelength and diagnosing emission of fluorescence at a wavelength. Alternatively, the fluorescent probe is AngioSense 750, the wavelength for illuminating the tooth is about 740 nm to about 760 nm, and the wavelength for detecting its fluorescence is about 770 nm to about 790 nm. Alternatively, the fluorescent probe is Genhance 750, the wavelength for illuminating the tooth is about 740 nm to about 760 nm, and the wavelength for detecting its fluorescence is about 770 nm to about 780 nm. Alternatively, the fluorescent probe is AngioSpark 750, the wavelength for illuminating the tooth is about 740 nm to about 760 nm, and the wavelength for detecting its fluorescence is about 770 nm to about 790 nm. Alternatively, the fluorescent probe is Alexa Fluor 750, the wavelength for illuminating the tooth is about 710 nm to about 730 nm, and the wavelength for detecting its fluorescence is about 760 nm to about 780 nm.

In yet another embodiment of the method, the fluorescence probe is Indocyanine Green, the wavelength for illuminating the tooth is about 750 nm to about 800 nm, and the wavelength for detecting its fluorescence is about 820 nm to about 870 nm. Alternatively, the fluorescence probe is a Doxorubicin, the wavelength for illuminating the tooth is about 400 nm to about 500 nm, and the wavelength for detecting its fluorescence is about 600 nm to about 700 nm. Alternatively, the fluorescence probe is a Riboflavin, the wavelength for illuminating the tooth is about 400 nm to about 500 nm, and the wavelength for detecting its fluorescence is about 500 nm to about 700 nm. Alternatively, the fluorescence probe is a Chlorophyll A, the wavelength for illuminating the tooth is about 600 nm to about 650 nm, and the wavelength for detecting its fluorescence is about 670 nm to about 900 nm. Alternatively, the fluorescent probe is a bacterial Chlorophyll, the wavelength for illuminating the tooth is about 650 nm to about 750 nm, and the wavelength for detecting its fluorescence is about 775 nm to about 825 nm. Alternatively, the fluorescence probe is a Porphyrin, the wavelength for illuminating the tooth is about 550 nm to about 650 nm, and the wavelength for detecting its fluorescence is about 650 nm to about 750 nm.

In an embodiment, the probe is a luciferase, luciferin and ATP, in which the wavelength for detecting its bioluminescence is about 600 nm to about 800 nm. Alternatively, the probe is a colloidal gold, and the wavelength for detecting an area of its absorbance is about 500 nm to about 800 nm. Alternatively, the probe is a bismuth, and the wavelength for detecting an area of its absorbance is about 500 nm to about 800 nm.

In general, illuminating the tooth involves illuminating light on an entire tooth surface, for example, scanning the surface with the beam of illuminating light. In yet another embodiment, the method involves illuminating the tooth surface at angles relative to the enamel prism, for example, an orientation parallel to the direction of the enamel prism or an orientation perpendicular to the direction of the enamel prism.

In another embodiment of the method, illuminating the tooth involves directing light through the occlusal layer of enamel. Alternatively, illuminating the tooth involves directing light to an interproximal area or adjacent to an interproximal area. In general, illuminating the tooth by directing light provides the anatomy of the tooth including the enamel, dentin, and enamel-dentin junction, and can be used to identify the size and location of caries bound to a probe.

In another aspect, the invention provides the invention provides a kit for detecting early stage dental caries in a subject, the kit including at least one probe selected from the group of: colloidal gold; a fluorescent probe; and a bioluminescent; such that the probe binds selectively to the caries, the kit further includes a container, and a positive control tooth sample having an early stage lesion.

In general, kit for detecting early stage dental caries in a subject includes a detectable probe that binds to the caries, a container, and a positive control tooth sample having an early stage lesion. In an embodiment of the kit, there are further included instructions for use, for example, instructions for use with an optical device. In various embodiments of the kit, the fluorescent probe is a tetracycline or a tetracycline conjugate. Alternatively the kit includes a fluorescent probe that is selected from the group consisting of OsteoSense 750, Cy7, CardioGreen (ICG), IR820 (ICG), Far-Green two, AngioSense 750, Genhance 750, AngioSpark, 750, Alexa Fluor 750, Indocyanine Green, Doxorubicin, Riboflavin, Chlorophyll A, bacterial Chlorophyll and Porphyrin. In another embodiment, the probe is at least one composition selected from the group of fluorescent and bioluminescent compositions. For example, the bioluminescent composition is at least one selected from the group of lucerifase, luciferin, and a mixture thereof, and the fluorescent composition is at least one composition selected from the group of OsteoSense 750, Cy7, CardioGreen (ICG), IR820 (ICG), Far-Green two, AngioSense 750, Genhance 750, AngioSpark, 750, Alexa Fluor 750, Indocyanine Green, Doxorubicin, Riboflavin, Chlorophyll A, bacterial Chlorophyll and Porphyrin. In another embodiment, the probe is at least one composition selected from the group of Qdot, colloidal gold, and bismuth. In yet another embodiment of the kit, the probe is a unit dose.

In general, the optical device is at least one device selected from the group of: a NIR light, a LED light, a hand-held intra-oral light wave detection device, a camera, and a fiber optic optical device connected to at least one detector selected from the group consisting of a CCD camera, an optical camera, and a spectrophotometer. In certain embodiments of the kit, the optical detection device further includes an electromagnetic wavelength radiation emitter, and a wavelength is generated for excitation of fluorescent probes.

A kit is provided herein for detecting early stage dental caries in a subject, the kit including a detectable probe, an optical device, and a container. Optionally included is a positive control tooth sample, such as an extracted tooth, having an early stage lesion.

In general, the kit in various embodiments includes an applicator for the probe, for example, selected from a syringe, a sprayer, a sponge, a bite wing plate, a gel, a strip, a plastic tape, a tray, a string, and other material well known to one of ordinary skill in the art of dentistry.

In another embodiment of the kit, the kit further includes a separator between teeth, for example, the separator is black or gray.

The kit in various embodiments further includes a syringe for delivering a fluid to remove the probe, for example, the fluid is a solution having at least one solute selected from the group consisting of hydrogen peroxide, phosphoric acid, sodium phosphate monobasic, sodium phosphate dibasic, methylene phosphoric acid, sodium chloride, potassium chloride, pyrophosphate dibasic, and pyrophosphate tetrabasic.

The invention now having been fully described is exemplified by the following examples and claims, which are exemplary only and are not intended to be construed as further limiting. The contents of all references cited are hereby incorporated herein by reference.

EXAMPLES

Example 1

Detection of Probe Fluorescence in Extracted Teeth Correlated with Presence of Caries To assess detection of caries using fluorescent probes, enamel samples from extracted teeth were analyzed to identify and obtain those samples having at least one "white spot" (100, FIG. 1 panel A) caries lesion. White spots were divided into two stages: visible white spots, and dull white spots on the enamel surface. Teeth were illuminated and examined for evidence of autofluorescence. No autofluorescence was observed in the teeth after illuminating them with ultra-violet light, therefore the possibility of using fluorescent agents to detect white spots was facilitated by this observation.

The enamel samples from extracted teeth were incubated in a tetracycline solution (1 mg/ml) for 60 seconds, and then were washed with phosphate buffered saline (PBS). The samples were tested using ultra-violet wavelength light of 260 nm (Ultra Violet lamp SB-4W). Fluorescence was determined using a hand-held device attached to an Olympus spectrophotometer. These teeth were observed to have a clear locus of bright yellow fluorescence. The locus of fluorescence was located in the area corresponding to the white spot identified by histological examination, indicating the tetracycline was bound to the white spot caries.

Example 2

Histological Analysis

Teeth having white spots were analyzed laterally by electron microscopy, and following obtaining transverse sections, regions of fluorescence were correlated with white spots caries. The teeth were also analyzed histologically to determine the absence or presence of early stage caries. The results were compared to areas observed to have fluorescence from the fluorescent probes.

Example 3

Detection of Caries in Bovine Teeth by Colloidal Gold Probes

To determine the capabilities of colloidal gold probes to detect caries, extracted bovine teeth were prepared using a model test system that includes etching the teeth with acid.

Bovine teeth were cleaned by soaking for 10 to 30 seconds in 10% hydrochloric acid. A model test system for caries was established by etching select surfaces with dental etching gel, non-silica 10% phosphoric acid etch gel, for 30 seconds. Control samples were retained in absence of etching.

Colloidal Gold Total Protein Stain (BioRad, Hercules, Calif.) was applied to each of the test samples and to the negative control samples, by soaking for 20-30 seconds. Samples were then rinsed with distilled water. Samples were further stained with Silver Stain Plus kit (Bio-Rad), derived from a method developed by Gottleib and Chavko (1997 Anal Biochem 165: 33). All tooth samples were then illuminated with near-infrared (NIR) light, for absorbance.

Results obtained indicated that the test samples that had been etched prior to soaking showed areas of silver-gray coloration. Controls not etched did not show any areas of coloration. The data show that NIR illumination of tooth samples contacted with a Gold probe detected early stage caries, including interproximal caries lesions.

Example 4

Detection of Caries in Human Subjects

Example herein describes a method of detecting early stage dental caries in a human subject using a tetracycline probe or a colloidal gold probe, respectively.

A dental patient is contacted via the buccal or lingual cavity with a solution of a tetracycline, such as a 1 mg/ml solution, as a gargle for 30 seconds. After extensive rinsing, the buccal or lingual cavity is illuminated with UV light, and respectively appearance and location of fluorescent spots, are probed with a hand-held attachment for a spectrophotometer. Areas of fluorescence or gray spots are photographed.

A dental patient is contacted via the buccal or lingual cavity with a solution of a colloidal gold, such as the BioRad Total Protein Stain, catalog number 170-6527, in order to soak the caries lesion and access the solution into the lesion. After gargling and extensive rinsing with water, the colloidal gold treatment is followed by a 20 second to 30 second gargle with Silver stain Plus (Bio-Rad). The buccal or lingual cavity is illuminated with near infra-red (NIR) light, and appearance and location of areas of gray-silver staining are probed with a hand-held attachment for a spectrophotometer. Areas of stain are photographed.

Example 5

Remineralization in Human Subjects of Early Stage Caries Detected by Optical Properties Following detection, procedures for remineralization are initiated at locations assessed as having early stage caries. For example, fluoride ions are introduced into the lesion by use of a topical gel or toothpaste formulated for this purpose. The remineralization treatments leading to restoration of integrity of the enamel induce precipitation of calcium and phosphate on crystals in the enamel that are partially demineralized.

Example 6

Assessment of Detection Probes Using Bovine Samples

Bovine teeth were obtained and sliced to obtain enamel samples. These enamel samples (having no dentin layer), were fabricated from these bovine teeth. A de-mineralized area was prepared by etching an area of the sliced enamel samples. The sliced enamel surface containing a de-mineralized area was contacted with concentrations of each of the probes. The surface was illuminated with wavelengths of excitation light and light of an emission wavelength was detected. Further, the absorbance of illuminating wavelengths was detected. Optical observations were obtained directly by eye, by spectrophotometer, or by camera such as photographing the tooth or indirectly by having the data sent from a device/sensor on an optical device to an imager on the optical device.

Example 7

Assessment of Detection Probes Using Interproximal Models of Extracted Human Teeth Interproximal models of extracted human teeth (molars and premolars) were fabricated using silicon impression materials. Interproximal enamel caries at about 500 nm depth and at about 1.5 mm depth were prepared by using areas of interproximal contact regions. The dental preparations having synthetic caries were assessed by radiographic films (bitewings) and a microscope.

A cotton ball was saturated with the detection probe, and placed in contact with the region of the interproximal enamel caries. The bound probe was observed by illuminating over a varying set of different wavelengths of excitation light, followed by detecting light of fluorescent emissions. Furthermore, absorbance of the illuminating wavelengths was detected as appropriate for each probe. Optical observations for each probe are shown in Table 1.

Figure 3:
FIG. 3 is a photograph showing absorption of light of a bismuth probe bound to an early stage caries lesion in a synthetic tooth preparation.
Figure 4:
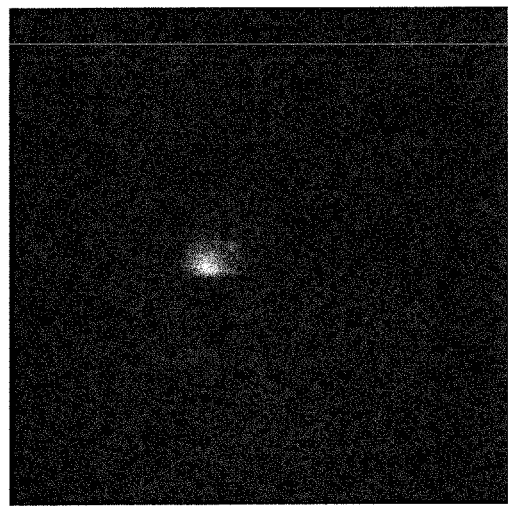
FIG. 4 is a photograph showing fluorescence of a Doxorubicin probe bound to an early stage caries lesion in a synthetic tooth preparation.
Figure 5:
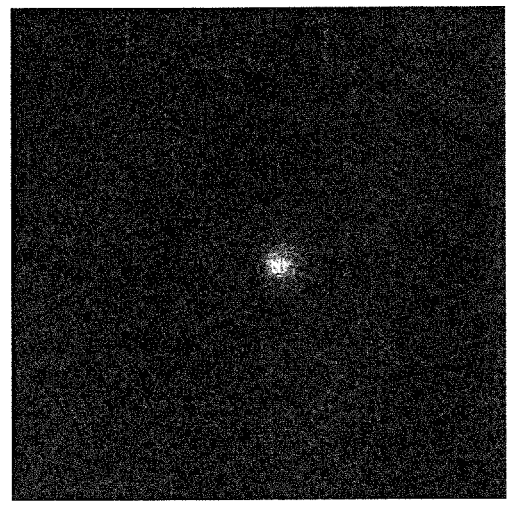
FIG. 5 is a photograph showing fluorescence of a Riboflavin probe bound to an early stage caries lesion in a synthetic tooth preparation.
Figure 6:
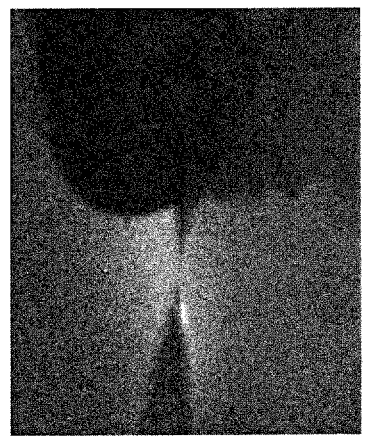
FIG. 6 is a photograph showing fluorescence of a Chlorophyll A probe bound to an early stage caries lesion in a synthetic tooth preparation.
Figure 7:
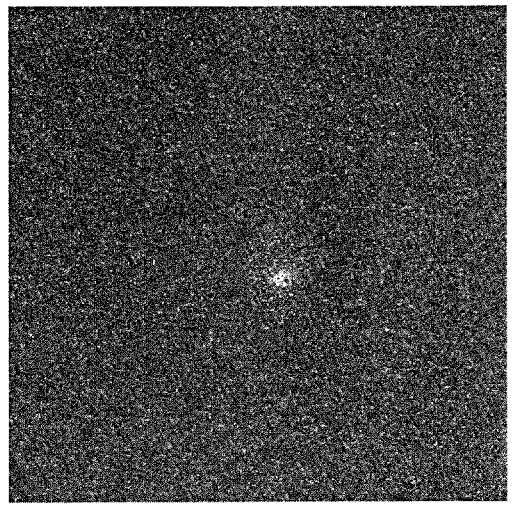
FIG. 7 is a photograph showing fluorescence of a Porphyrin probe bound to an early stage caries lesion in a synthetic tooth preparation.
Figure 8:
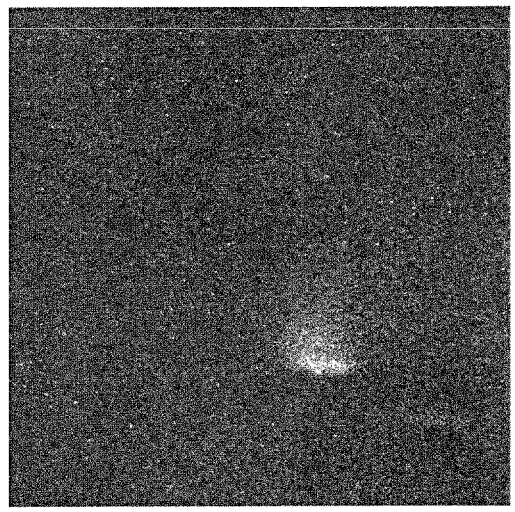
FIG. 8 is a photograph showing bioluminescence of a luciferase and luciferin probe bound to an early stage caries lesion in a synthetic tooth preparation.
Figure 9A:
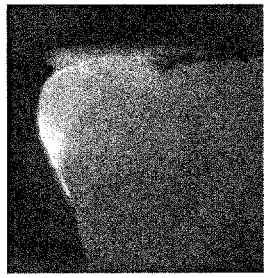
FIG. 9 is a set of photographs showing fluorescence of each of OsteoSense 750 (panels A, B, C and F), AngioSense 750 (panel D), Genhance 750 (panel E), and Chlorophyll A (panel G) probes bound to interproximal caries on teeth.
Figure 9B:
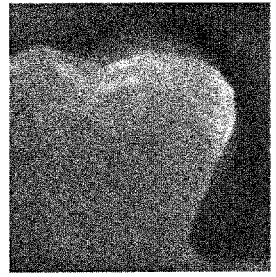
Figure 9C:
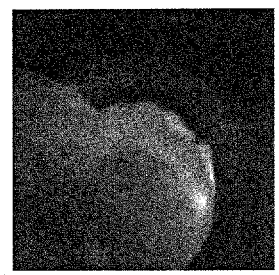
Figure 9D:
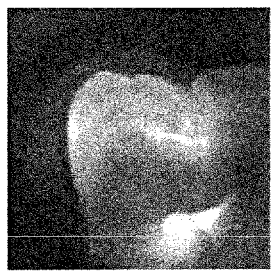
Figure 9E:
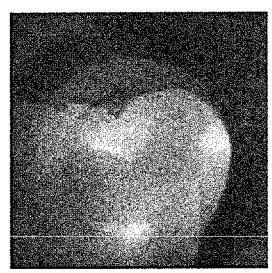
Figure 9F:
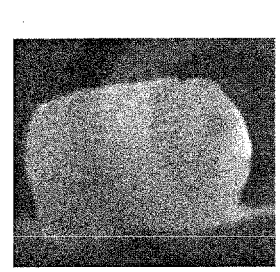
Figure 9G:
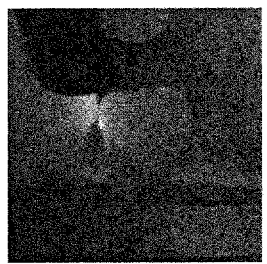

Each tooth preparation having interproximal enamel caries and bound probe was illuminated and photographed. Absorption of light was observed on a tooth preparation with an early stage caries lesion to which a preparation of a bismuth probe has been bound (FIG. 3). Fluorescence of an early stage caries lesion was observed in a tooth preparation to which a preparation of a Doxorubicin probe had been bound (FIG. 4), a Riboflavin probe had been bound (FIG. 5), a Chlorophyll A probe has been bound (FIG. 6), and a Porphyrin probe has been bound (FIG. 7). Bioluminescence of an early stage caries lesion was observed in a tooth preparation to which has been bound a probe preparation having luciferase and luciferin (FIG. 8).

Example 8

Determination of Variables

Probes were tested for appropriate concentration, kinetics of binding and retention. Intensity of the illumination light, and the size of the illumination light beam were varied, and data were recorded for each probe. Interproximal caries were observed by contacting caries with each of OsteoSense 750, AngioSense 750, Genhance 750, and Chlorophyll A, illuminating the tooth with light of an excitation wavelength, and detecting light of an emission wavelength (FIG. 9). The concentration of each probe was varied to determine an optimum concentration for binding during a time period suitable for dental use. Durations of contacting were also tested, for example about 10 seconds, about 20 seconds, about 40 seconds, or about 60 seconds.

TABLE 1

Properties of detection probes

| detection probe | composition type | detection type | excitation/ absorbance wavelength (nm) | emission wavelength (nm) | degree of detection |
|---|---|---|---|---|---|
| Bismuth | Metal | Absorbance | Absorption | | Good |
| Gold colloid | Metal colloid | Absorbance | 530 | | Weak |
| Doxorubicin | Anti-cancer medicine | Fluorescence | 480 | 630 | Good |
| Riboflavin | Vitamin B$_2$ | Fluorescence | 450 | 550-700 | Good |
| Chlorophyll A | Chlorophyll | Fluorescence | 614 | 670-900 | Good |
| Indocyanine Green | Dye | Fluorescence | 800 | 835 | Weak |
| Porphyrin | | Fluorescence | 600 | 700 | Good |
| Luciferase/ Luciferin | Organic enzyme and protein | Chemical reaction fluorescence | | 630 (PH) dependent | Good |
| Qdot | Nanodot | Fluorescence | 400-750 | 750-900 | Good |
| HiLyte Fluor | Small molecular weight compound | Fluorescence | 720-750 | 750-800 | Good |
| Bacterial Chlorophyll | Chlorophyll | Fluorescence | 650-750 | 775-285 | |
| OsteoSense 750 | Dye | Fluorescence | 740-760 | 770-790 | Very Good |
| CardioGreen (ICG) | Dye | Fluorescence | 750-800 | 820-870 | Good |
| IR820 (ICG) | Dye | Fluorescence | 745 | 845 | Good |
| Cy7 | Dye | Fluorescence | 700-770 | 760-800 | |
| Far-Green two | Dye | Fluorescence | | | |
| AngioSense 750 | Dye | Fluorescence | 740-760 | 770-790 | Weak |
| Genhance 750 | Dye | Fluorescence | 740-760 | 770-780 | Weak |

TABLE 1-continued

Properties of detection probes

| detection probe | composition type | detection type | excitation/ absorbance wave- length (nm) | emission wave- length (nm) | degree of detect- ion |
|---|---|---|---|---|---|
| AngioSpark 750 | Dye | Fluorescence | 740-760 | 770-790 | Weak |
| Alexa Fluor 750 | Dye | Fluorescence | 710-730 | 760-780 | Good |

Binding of the probes to the surface of a tooth having different occlusal cavity conditions were also determined, e.g., plaque, gingival, calculus.

Figure 10A:
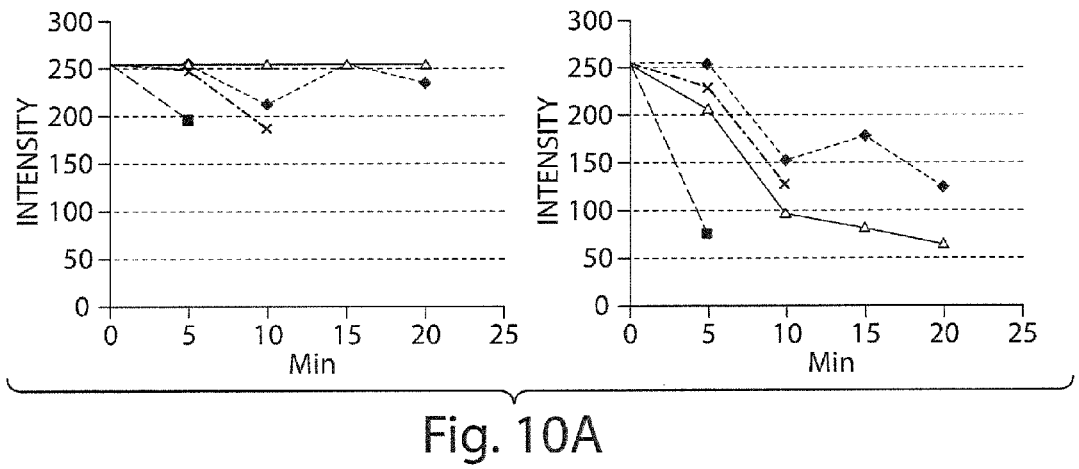
FIG. 10 is a set of graphs showing quantification of fluorescence intensity (ordinate) of probes in a deep lesion (spot#1, left graphs) and a shallow lesion (spot #2, right graphs) and amount on time in minutes the fluorescence intensity was detected (abscissa). Panel A and panel B show fluorescent intensity results for probes diluted 1:100 and 1:10, respectively. The probes contacted and bound to the lesions are CardioGreen (diamonds), IR820 (rectangles), Cy7 (triangles), and OsteoSense 750 (-x-).
Figure 10B:
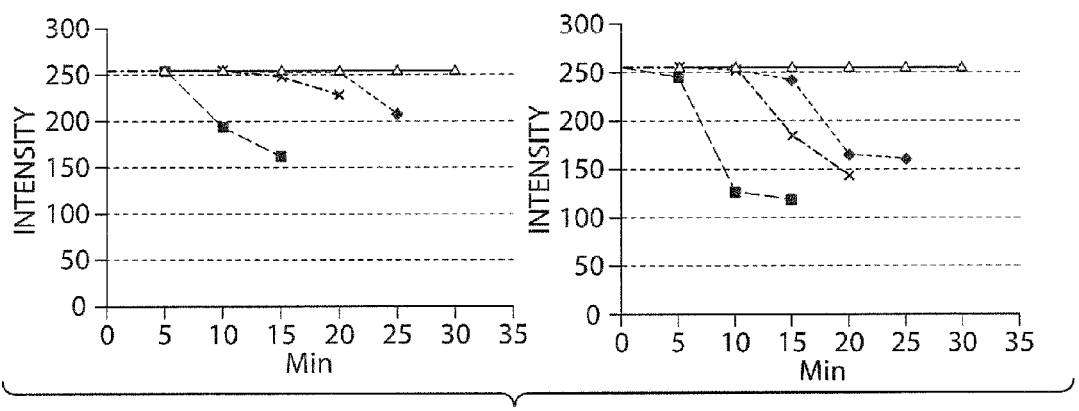
Figure 11A:
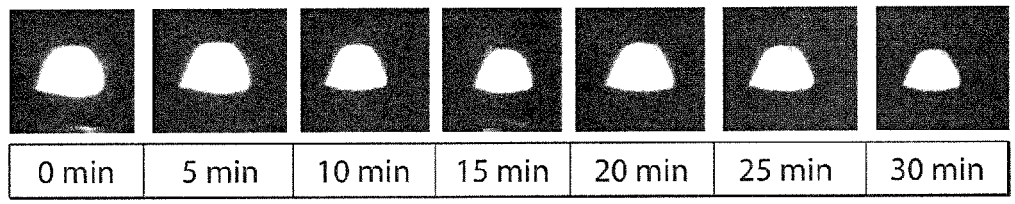
FIG. 11 is a set of photographs that shows fluorescence over a period of time (minutes, min) of probes (Cy7, OsteoSense 750 and IR(820)) bound to caries lesions on demineralized enamel surfaces.
Figure 11B:
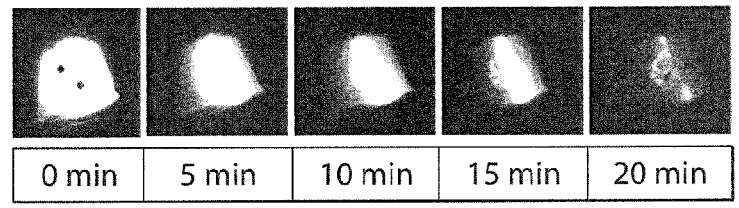
Figure 11C:
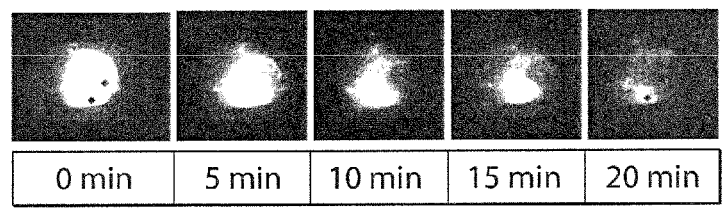
Figure 11D:
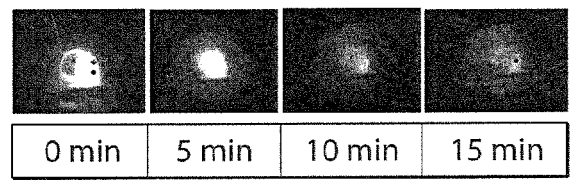

Data showed that multiple dilutions and concentrations of the probes could be used to bind and to detect early stage caries. Dilutions (1:10 and 1:100 dilutions from a 1 mg/mL stock solution) of each of CardioGreen (ICG), IR 820 (ICG), Cy7, and OsteoSense 750, and probe bound to caries were prepared, and tested for intensity of and duration of fluorescence. See FIG. 10 and FIG. 11. It was observed from the data that images of Cy7 diluted 1:10 and images of CardioGreen diluted 1:10 showed similar fluorescence between 0 min and 15 min on both shallow and deep lesions. Images of Cy7 diluted 1:10 retained much greater intensity in both deep and shallow lesions compared to images of CardioGreen (ICG) diluted 1:10. Images of CardioGreen (ICG) and images of Cy7 were observed to produce greater fluorescent intensity at each concentration and lesion depth compared to IR820 (ICG). OsteoSense 750 diluted 1:100 was observed to produce greater intensity than IR820 even when diluted 1:10 (FIG. 11).

Example 9

Application to Caries Using a Wedge for Delivery

The Example herein shows a probe was applied to a tooth having an interproximal caries lesion using a delivery device and the probe with bound caries was detected optically.

Figure 12A:
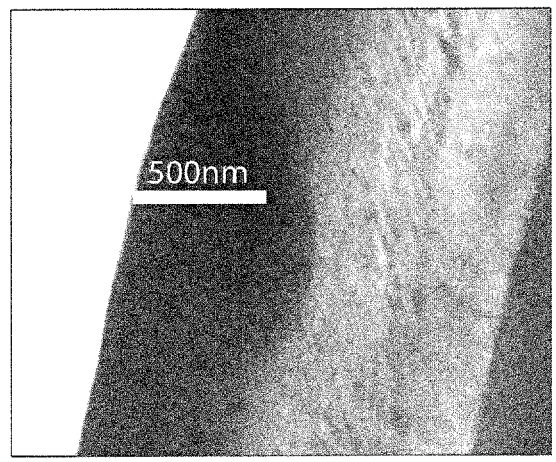
FIG. 12 is photograph of a tooth with caries lesion that was contacted with a fluorescent probe using a syringe and imaged with a light microscope (panel A) and a fluorescent microscope (panel B). Comparison of the images shows that the fluorescent probe was delivered into and detected the area, size and depth of the caries lesion. A bar indicates 500 micrometers (μm).
Figure 12B:
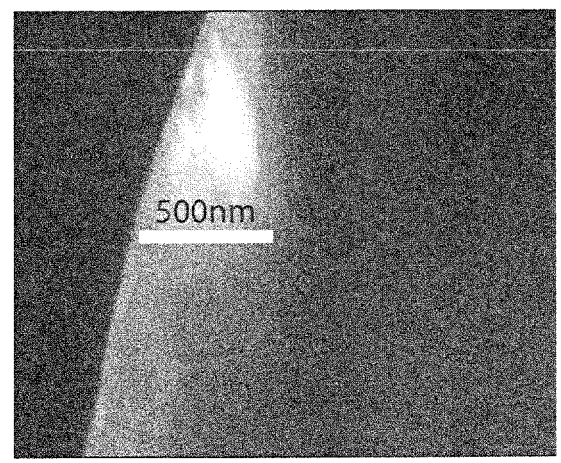

A fluorescence probe was contacted/inserted into a caries lesion using a wedge type of delivery tool. The probe was placed on the outside of the wedge and was then inserted between the teeth. Data shows that probe was successfully infiltrated into almost the entire area of the caries (compare FIG. 12 panel A and FIG. 12 panel B).

Figure 13A:
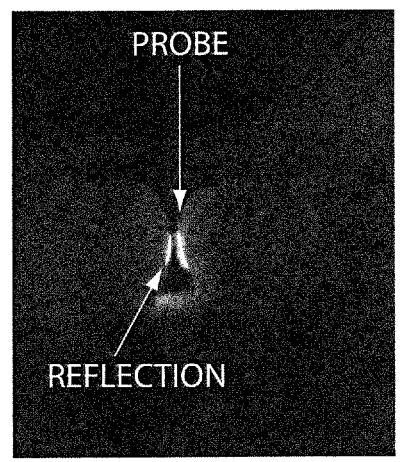
FIG. 13 is a set of photographs showing each of: detection of fluorescence caused by reflection of a probe bound to a caries lesion on an adjacent tooth (panel A), placement of a separator to eliminate the reflection fluorescence on the adjacent tooth (panel B), and corresponding elimination by the separator of fluorescence caused by reflection of a probe bound to a caries lesion on an adjacent tooth (panel C).
Figure 13B:
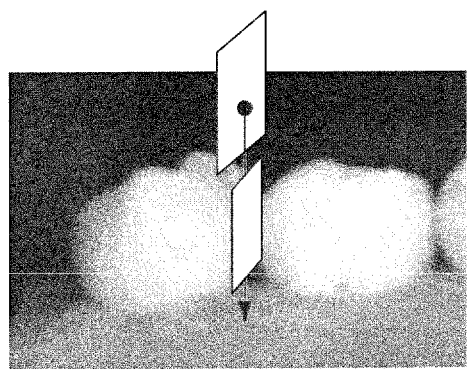
Figure 13C:
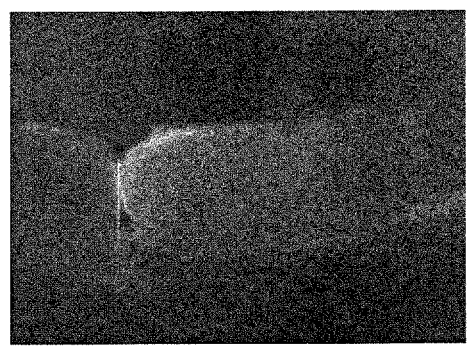
Figure 14A:
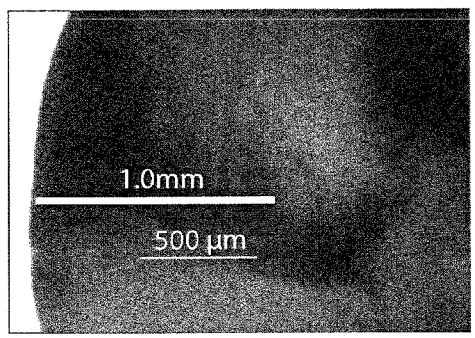
FIG. 14 is a set of photographs showing a light microscope image of a tooth with a caries lesion (panel A), a fluorescent microscope image of the tooth having OsteoSense 750 bound to the caries lesion (panel B), and a fluorescent microscope image of the tooth three minutes (panel C) and 10 minutes (panel D) after adding hydrogen peroxide (38%, Ultradent Products Inc., South Jordan, Utah) to remove OsteoSense 750 from the tooth. Bars indicate 500 micrometers (μm) and one millimeter (mm).
Figure 14B:
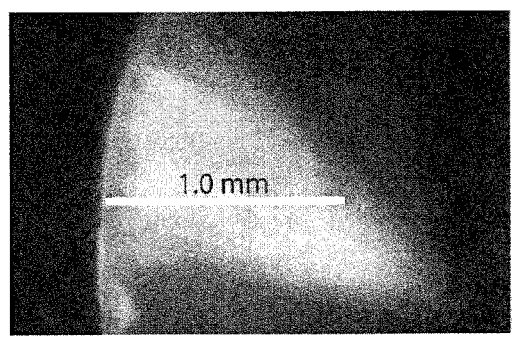
Figure 14C:
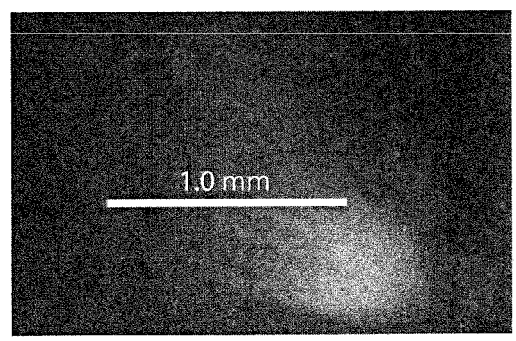
Figure 14D:
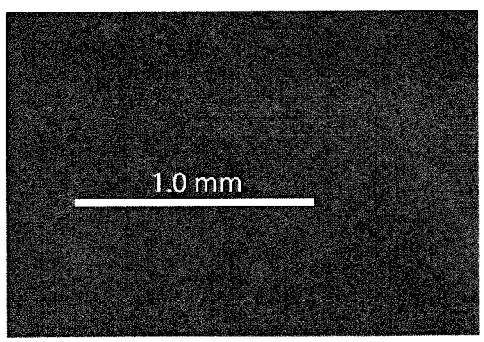

Fluorescence was observed on an adjacent tooth because of the reflection of a fluorescence of a tooth having a fluorescent probe bound to a caries lesion (FIG. 13 panel A). A black/gray separator was placed between the teeth and it was observed that the separator eliminated reflection of fluorescence to the tooth not having an early stage dental caries (FIG. 13 panels B and panel C).

Example 10

Removal of Probe from Two Model Systems: Extracted Teeth and Hydroxyapatite

Methods were tested for removing OsteoSense 750 bound to a tooth or to hydroxyapatite. The efficacy of removal of the probe by the solution was determined by criteria such as extent of fluorescence remaining on a tooth after rinse, or fluorescence extracted from hydroxyapatite into a rinse solution.

A caries lesion was identified on a tooth by light microscopy (FIG. 14 panel A) and the optical detection system using OsteoSense 750 and fluorescence microscopy (FIG. 14 panel B). The tooth was rinsed with a solution of hydrogen peroxide (38%, Ultradent Products Inc.). Three minutes after application of the hydrogen peroxide, the fluorescence of the probe bound to the tooth was observed to be substantially reduced (FIG. 14 panel C). Ten minutes after application of the solution of hydrogen peroxide, fluorescence indicating presence of the bound probe was substantially eliminated (FIG. 14 panel D). Thus, hydrogen peroxide was shown to be effective for removing OsteoSense 750 bound to caries.

Samples of hydroxyapatite (HA) and a volume of OsteoSense 750 were mixed in a tube. Solutions of each of hydrogen peroxide (30%), phosphoric acid (40%), or control, water, were added to a sample in a tube. The tubes were vortexed, and the mixture was allowed to settle to obtain a supernatant. Each supernatant was collected and analyzed for probe content using a spectrophotomer. A spectrometric signal at about 750 nm indicates a release of OsteoSense 750 that was bound to the HA. Supernatants from each of the water control and from hydrogen peroxide were observed to result in no signal at 750 nm. Data showed that the phosphoric acid solution supernatant resulted in a definite peak at 750 nm. Thus, data show that phosphoric acid was effective for removing OsteoSense 750 from hydroxyapatite.

Another method using hydrogen peroxide for removal of probe was tested in this Example, rinsing the hydroxyapatite or the tooth with saline (PBS) prior to treatment with hydrogen peroxide, and measuring absorbance to determine OsteoSense 750 removal at each step.

The efficacy of hydrogen peroxide was determined by comparing absorbance values at 750 nm for hydrogen peroxide rinse solutions, phosphate buffered saline (PBS) wash solutions, and control solutions. An absorbance at 750 nm within a spectrophotometric scan of 550 nm to 850 nm indicates a presence of OsteoSense 750 in each mixture. A control absorbance value at 750 nm for OsteoSense 750 diluted 1:100 in PBS was shown to be 0.337 and was used as a standard for purposes of calculations.

A sample of hydroxyapatite was contacted in a tube with a volume of OsteoSense 750 (1:100 dilution in PBS). The HA sample was washed with PBS and a spectrophotometric scan of the wash solution was performed. The absorbance at 750 nm was 0.036 for the wash solution. The HA sample was rinsed with a volume of hydrogen peroxide and a spectrophotometric scan of the hydrogen peroxide rinse solution was performed. The absorbance at 750 nm was 0.252 for the hydrogen peroxide fluid. A spectrophotometric scan was performed for a control solution of OsteoSense 750 diluted 1:100 in hydrogen peroxide, the absorbance value at 750 nm was 0.273.

A comparison of the absorbance values at 750 nm showed the presence of greater amounts of OsteoSense 750 in the hydrogen peroxide fluid compared to the PBS washes. Thus, hydrogen peroxide was effective for removing OsteoSense 750 that was bound to hydroxyapatite.

To further determine the efficacy of hydrogen peroxide (38%, Ultradent Products Inc.) for removing OsteoSense 750, five teeth having a caries lesion were contacted with a volume (1 µL) of OsteoSense 750, applied to a caries present on each tooth. The OsteoSense 750 (0.5 µL) was then collected from each tooth surface, and added to 100 µL of de-ionized water. A spectrophotometric scan was performed for each of these OsteoSense 750 solutions to determine binding differentially. Each tooth was then wiped with material to remove residual OsteoSense 750 from the tooth, and washed twice with PBS (150 μL volume for each wash). The first and the second wash solution for each tooth were collected and analyzed using spectrophotometric scans, absorbance values at 750 nm were observed for the first PBS wash solutions. Absorbance values showed no probe present in the second PBS wash solutions.

A volume of hydrogen peroxide (2 μL of a 1:20 dilution in de-ionized water) was applied for one minute to the area of the tooth having the caries, 150 μL of PBS was added to each of the areas, and the hydrogen peroxide mixture was collected. Spectrophotometric scans were performed on these mixtures and showed background absorbance at 550 nm and at 850 nm. A representative absorbance value at 550 nm was subtracted from absorbance values at 750 nm for each hydrogen peroxide mixture.

Data analyses of the absorbance data at 750 nm included calculating absorbance of OsteoSense 750 after staining teeth, after uptake in caries, in PBS washes, and in hydrogen peroxide mixtures. The decay/reduction of absorbance values at 750 nm resulting from applying hydrogen peroxide to OsteoSense 750, and corrected absorbance values were calculated. Data show that hydrogen peroxide removed 80% to 93% of OsteoSense 750 from the caries (Table 2).

The optical devices were: NW light source (Xenon light source MAX 301, Asahi Spector, Japan) with a filter that produces an excitation wavelength of about 740 nm; CCD detector camera (MC285SPD-L0B0, Texas Instrument, USA) that receives light through a 790 nm filter to detect fluorescent emission wavelength at about that wavelength; platform to stabilize specimens (Suruga, Japan); and image analysis software (Capture Base, Japan).

Figure 15A:
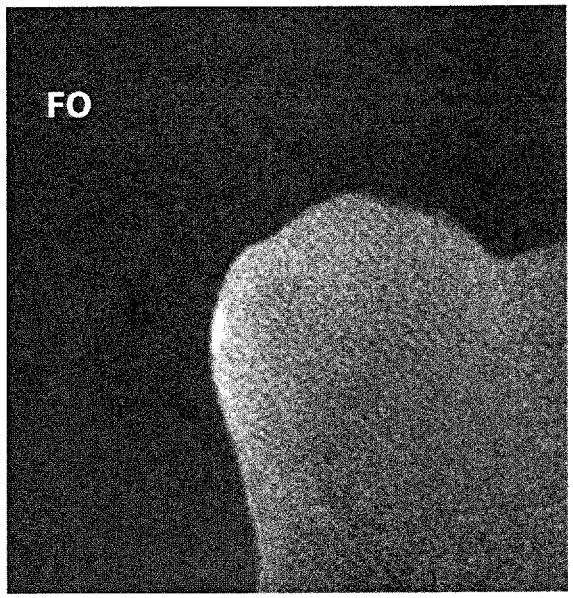
FIG. 15 is a set of photographs showing detection of fluorescence of OsteoSense 750 probe bound to caries lesions in human extracted teeth. The teeth were contacted with OsteoSense 750 probe, illuminated with near infrared light at 740 nm wavelength through the occlusal layer of enamel (FO; panel A), or at the interproximal area (FI; panel B), and detected for fluorescence emission.
Figure 15B:
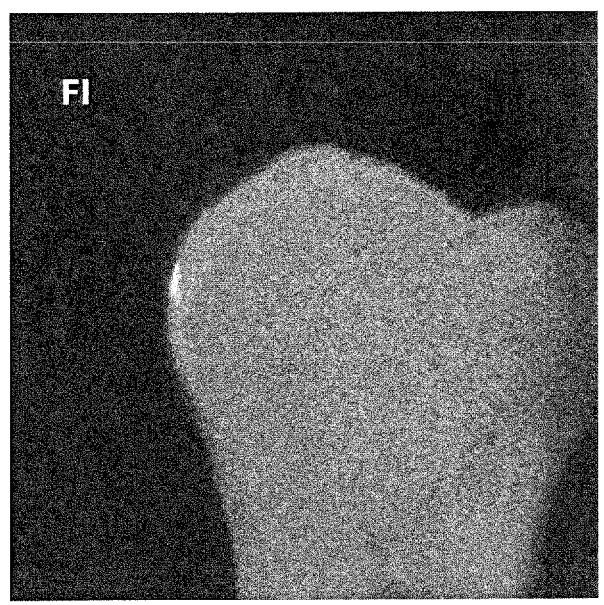

NW light (740 nm) was used to illuminate teeth from two different directions. Teeth were illuminated by NIR light either indirectly by exciting the interproximal area through the occlusal layer of enamel (FO) or directly by exciting the interproximal area (FI). Emission light signals were then captured from the buccal surface of teeth with a detector-filter (790 nm). Representative data is shown in FIG. 15. Bitewing X-ray images of the teeth were obtained in addition to the occlusal illumination and interproximal illumination images. Data were obtained from eleven dentists who evaluated the X-ray, occlusal illumination and interproximal illumination images, and each assessment for a tooth was recorded either as a No Lesion or a Lesion.

TABLE 2

Absorbance data (750 nm) showing efficacy of hydrogen peroxide to remove OsteoSense 750 from teeth having caries

| Solution | Absorbance at 750 nm | | | | |
| --- | --- | --- | --- | --- | --- |
|  | tooth A | tooth B | tooth C | tooth D | tooth E |
| OsteoSense OD750 after stained tooth[a] | 0.3438 | 0.2986 | 0.1562 | 0.242 | 0.2574 |
| OsteoSense 750 uptake in caries[b] | 0.1836 | 0.2288 | 0.3712 | 0.2854 | 0.27 |
| PBS wash[c] | 0.01245 | 0.0087 | 0.0135 | 0.0195 | 0.00525 |
| hydrogen peroxide rinse[d] | 0.0246 | 0.0378 | 0.01425 | 0.0138 | 0.01395 |
| decay of OsteoSense750 at 1 min by hydrogen peroxide[e] | 0.0727/0.3989 = 1/5.49 | | | | |
| corrected absorbance of hydrogen peroxide mixture[f] | 0.135054 | 0.207522 | 0.078233 | 0.075762 | 0.076586 |
| % OsteoSense 750 removed[g] | 80 | 80 | 93 | 88 | 93 |
| OD750 of OsteoSense750 (1 μl in 100 μl dw[h]) | 0.5274 | | | | |

OsteoSense750 uptake in caries is h minus a hydrogen peroxide absorbance correction is d times 5.49
% washed (g) is 100 minus (100 times ((b plus f) divided by a))

Thus, data show that hydrogen peroxide was effective for removing OsteoSense 750 bound to hydroxyapatite and OsteoSense 750 bound to caries on teeth.

Example 11

Sensitivity, Specificity, Predictive Value of the Optical Detection System

This example was performed to determine whether the optical detection system herein provides constant and reliable results for accurate representation of caries depth and location.

Data were obtained from 33 extracted human permanent premolars and molars characterized as free of restorations. These 33 teeth were found to contain ten white spots and eleven cavitated lesions. Twelve teeth were free of lesions.

An interproximal surface of each tooth was used for this example and was numbered in a random order. OsteoSense 750 (1 μl of 1:100 dilution) was applied to the interproximal areas of each tooth for 10 seconds, and teeth were washed with distilled water and gently wiped with a gauze (2×2).

Figure 16A:
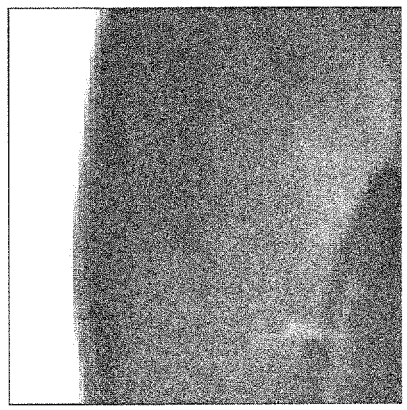
FIG. 16 is a set of photographs showing histological examination of teeth for caries and identified with a light microscope as having No Lesion (panel A) or Lesion (panel B).
Figure 16B:
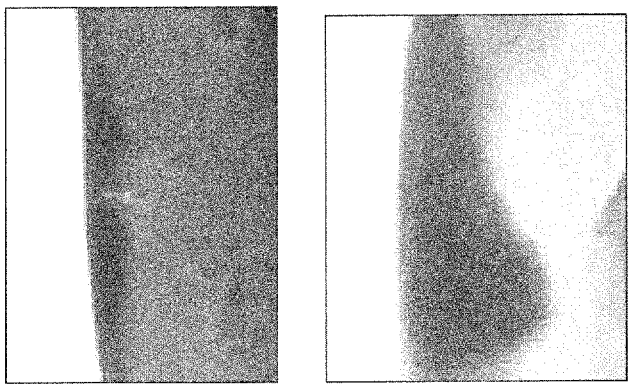

Each tooth was then prepared and polished using Vector Powerhead (Buehler, USA) from the buccal and lingual surfaces into 1 mm sections. Each surface was then examined by light microscope (Four-fold magnification; Olympus, USA) for histological examination, which is recognized as a gold standard method by present clinicians to determine the presence of caries in teeth. Using the histological examination, the teeth were recorded in categories as No lesion or Lesion. FIG. 16 shows representative histological data.

Sensitivity, specificity, positive predictive value (PPV), and negative predictive value (NPV) were calculated for each of the three methods using the data from these determinations. Assessment by the evaluators of the three methods was compared with the results obtained by histological examination. Lesions were observed to be present in 23 of 33 interproximal surfaces as determined by histological examination.

The data in Table 3 showed that the optical detection system described herein is characterized by higher sensitivity and NPV that those of the other method, X-rays. Sensitivity and NPV were observed to be, for each type of imaging, statistically significant. The specificity and PPV between any two methods were found to be statistically insignificant.

Sensitivity as used herein describes the percentage of teeth with early stage dental caries (i.e., teeth with a caries lesion within less than one-half depth of enamel) as determined by histological examination and later identified by each method as having caries. Specificity as used herein describes percentage of teeth which did not have early stage caries as determined by histological examination and were identified by each method as no caries.

The inter-examiner reliability (Fleiss' kappa values) of each of occlusal illumination and interproximal illumination, respectively, was 0.77 and 0.66. This compares to inter-examiner reliability of 0.28 for X-rays. The data showed that there was less variability in the evaluators' determinations of caries presence on a tooth using the optical detection systems described herein compared to bitewing X-rays. These data show that clinicians using this optical detection system will be able to make a best possible diagnosis compared to other systems.

TABLE 3

Statistical analysis: sensitivity, specificity, PPV and NPV

| method (abbreviation) | sensitivity* | specificity | PPV | NPV* |
|---|---|---|---|---|
| X-ray (XR) | 0.32 (0.20, 0.44) | 0.845 (0.78, 0.91) | 0.853 (0.43, 1.00) | 0.348 (0.18, 0.52) |
| Occlusal illumination (FO) | 0.715 (0.56, 0.87) | 0.9 (0.76, 1.00) | 0.947 (0.87, 1.00) | 0.584 (0.35, 0.82) |
| Interproximal illumination (FI) | 0.893 (0.81, 0.98) | 0.764 (0.57, 0.95) | 0.9 (0.80, 1.00) | 0.775 (0.57, 0.98) |

*indicates statistical significance

Example 12

Early Caries Detection Performance of the Optical Detection System

The ability of the caries detection system to detect early stage caries was assessed using 24 extracted human permanent premolars and molars which had a white spot. One interproximal surface of each tooth was used for the experiment and surfaces were numbered randomly. OsteoSense 750 (1 μl of 1:100 dilution) was applied to the interproximal areas of each tooth for 10 seconds, and these areas were washed with distilled water and gently wiped with a gauze. The optical device system used to examine the teeth was described in Example 11.

NIR light (740 nm) illuminated teeth from two different directions, occlusal illumination, FO, or interproximal illumination, FI. Emission light signal were then captured from the buccal surface of teeth with a detector-filter (790 nm). X-ray images of the teeth were also obtained.

Data were obtained from six dentists who evaluated the X-ray, occlusal illumination and interproximal illumination images, and each assessment was recorded either as a No lesion, or as a Lesion, with a Lesion being less than one-half enamel depth, or a Lesion with more than one-half enamel depth.

Histological examination of the teeth was performed for each tooth and determined that the 24 teeth had caries with demineralization that extended less than one-half depth of the enamel, i.e., caries lesion (FIG. 16).

Each assessment was categorized into the following statistical categories: a Match, an underestimation (UE) or an overestimation (OE), by comparing the result to the histological results. Histological examination determined that all the teeth had early caries, defined as lesions with a depth less than one-half enamel depth. Thus, an assessment using X-ray, occlusal illumination, and interproximal illumination images of a lesion with depth less than one-half enamel depth was categorized as a Match. Assessment of no lesion by X-rays, occlusal illumination, and interproximal illumination was categorized as an underestimation (UE) of the true lesion size by histological examination, and X-rays, occlusal illumination, and interproximal illumination assessment of Lesion with depth more than one-half enamel depth was categorized as an over estimation (OE) of the true lesion size by histological examination.

Statistical analysis was performed using the SAS version 9.1 statistical package (SAS Institute, USA). A formal comparison of the diagnostic methods was achieved using a Mixed-effects multinominal logistic regression model. See Table 4 and Table 5.

TABLE 4

Mean values and standard deviations of the X-rays, occlusal illumination and interproximal illumination

| method (abbreviation) | Match | Underestimation | Overestimation |
|---|---|---|---|
| X-ray (XR) | 11.81 (7.18) | 79.17 (13.18) | 9.03 (8.09) |
| Occlusal illumination (FO) | 29.17 (9.50) | 53.47 (8.09) | 17.36 (4.10) |
| Interproximal illumination (FI) | 64.58 (9.03) | 13.89 (6.80) | 21.53 (4.87) |

A statistically significant difference in the odds ratios was observed for an underestimated (UE) misclassification compared to a Match for observations by evaluators of occlusal illumination images or interproximal illumination images compared to X-ray images. There was no statistically significant difference in the odds ratios for an overestimated (OE) misclassification compared to a Match when examiners used occlusal illumination or interproximal illumination images compared to X-ray images. The inter-examiner reliability (Fleiss' kappa values) for occlusal illumination was calculated to be 0.68 and for interproximal illumination was calculated to be 0.51 compared to only 0.15 for X-rays. The overestimated errors were observed to be statistically insignificant between the systems. These data show that the methods of optical detection herein are significantly improved with respect to underestimated errors compared to traditional X-rays and that early stage dental caries were successfully detected.

TABLE 5

Statistical analysis of X-ray, occlusal illumination, and interproximal illumination images as compared to histological examination

| outcome categories compared | methods compared | odds ratio for comparing two methods | P value |
|---|---|---|---|
| UE* and Match | Occlusal illumination and X-ray | 0.2703 | 0.0100* |
| | Interproximal illumination and X-ray | 0.0309 | 0.0002* |
| OE* and Match | Occlusal illumination and X-ray | 0.7697 | 0.5843 |
| | Interproximal illumination and X-ray | 0.4205 | 0.0975 |

*indicates statistical significance

Example 13

Comparison of the Size of a Caries Lesion Identified by a Probe to Actual Size of the Caries Lesion Data were obtained to determine the accuracy between by the optical detection system as compared to the true depth of a caries lesion as determined by a standard method.

A five millimeter section was obtained from each of 33 extracted human teeth by grinding from the buccal and/or lingual side. OsteoSense 750 (1 µl of 1:100 dilution) was applied to the interproximal areas of each section for 10 seconds. These interproximal areas were washed with distilled water and gently wiped with gauze. Light microscope images of the teeth were obtained. The teeth were illuminated with NIR excitation light (740 nm) and the fluorescent signal from the carious lesions were detected and pictured using a fluorescent microscope with an emission filter (790 nm).

Figure 17A:
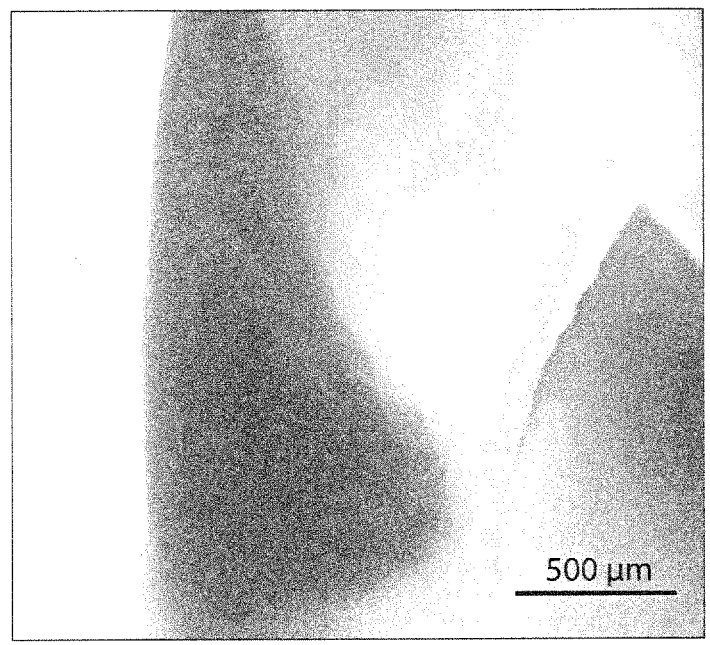
FIG. 17 is a set of photographs showing a light microscope image of the depth of a caries lesion in a tooth (panel A), and a fluorescent microscope image of the same tooth having OsteoSense 750 bound to the caries (panel B). Comparison of the photographs shows that the fluorescent probe/optical detection method delineates the depth of the caries. Bars indicate 500 micrometers (μm).
Figure 17B:
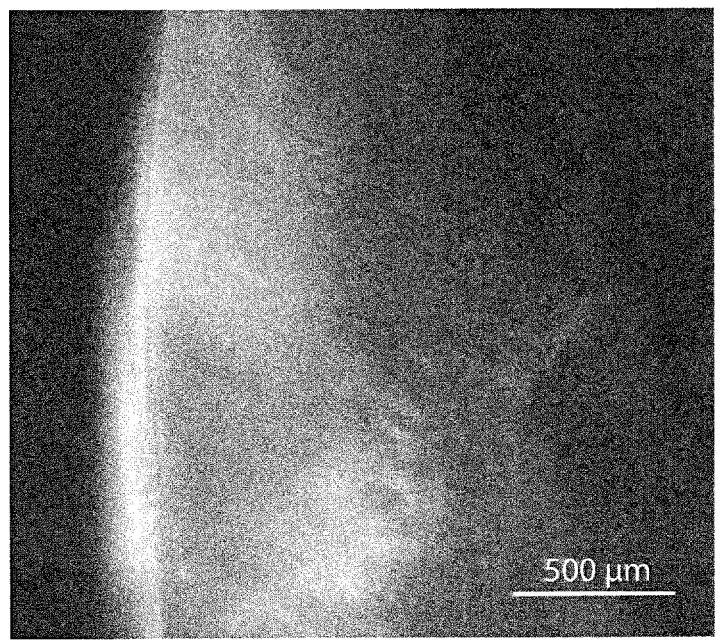

The fluorescence microscope data showed the depth determined by OsteoSense 750 in the optical detection system, while the light microscope showed the actual caries depth (or the best means of measuring the true depth). A representative set of teeth analyzed in this manner is shown in FIG. 17. Analysis of the images showed that the depth of the lesions was 0.2 mm to 1.5 mm, the average filtration extent was 93.72±14.5% and the correlation coefficient was −0.002.

Data obtained in this example showed that the optical detection system delineated about 93% of the true size of the caries and that there was no significant correlation between infiltration extent and the depth of the carious lesion. Thus, the optical detection system using OsteoSense 750 was shown to be effective in identifying the true depth of caries in human extracted teeth.

Figure 18A:
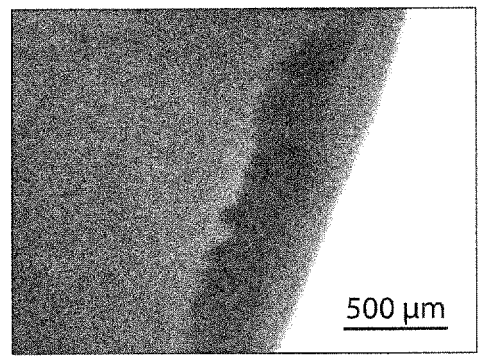
FIG. 18 is a set of photographs of a light microscope image of the actual depth of a caries lesion in a tooth (panel A), a fluorescent microscope image of OsteoSense 750 bound to the caries lesion (panel B), and a fluorescent microscope image of the tooth after adding hydrogen peroxide (38%, Ultradent Products Inc.) to remove OsteoSense 750 from the lesion (panel C).
Figure 18B:
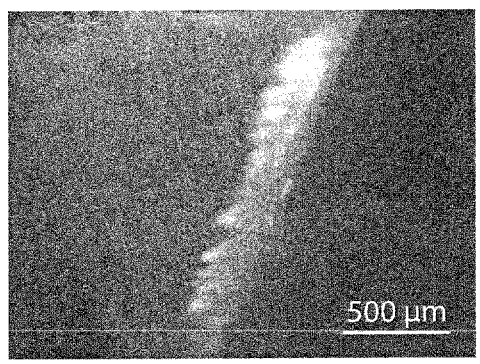
Figure 18C:
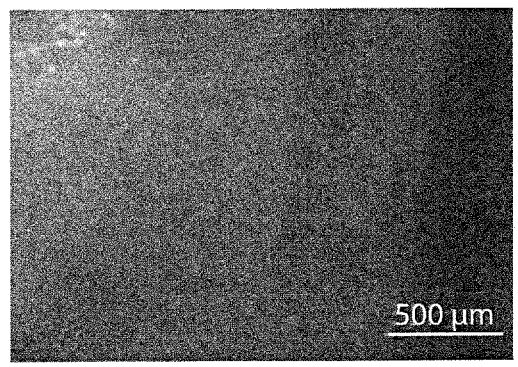

Images of teeth with caries lesions bound to OsteoSense 750 were taken using a light microscope and the optical detection system. Hydrogen peroxide (38%, Ultradent Products Inc.) was applied with a syringe to the caries lesion. This solution was observed to have eliminated fluorescence (FIG. 18). Thus, hydrogen peroxide was found to be effective for removing a fluorescent probe bound to caries lesions on human teeth as detected using the optical system.

Example 14

RFU Comparison of Efficacy of Solutions to Release from OsteoSense 750 from HA A comparison of efficacy of solutions of various agents to release OsteoSense 750 from hydroxyapatite was tested. Variables included conditions of pH, temperature, and presence of 1% calcium chloride. Prior to testing the efficacy of the solutions to release OsteoSense 750 from hydroxyapatite, a standard curve was prepared to obtain a linear region for correlation of relative fluorescence value with concentration of OsteoSense 750.

The standard curve was prepared using dilutions of OsteoSense 750 (1:100, 1:200, 1:400, 1:800, and 1:1000 of a 1 mg/mL stock solution), diluted in wells; a volume (90 µL) of each was collected, and fluorescence was measured using a fluorometer. The observed relative fluorescence units (RFU) were plotted as a function of a relative concentration (1:1000 to 1:100), and a linear relationship was observed. Relative fluorescence units observed in amounts were from about 10 at the 1:1000 dilution to about 110 at the 1:100 dilution. Further, the RFU of 1:300 dilution was observed to be 37.5 RFU. Further data obtained from examples herein used this curve to obtain amounts, and examples included a standard dilution of 1:300 of OsteoSense 750.

To compare efficacy of various agents to release OsteoSense 750 from hydroxyapatite, a sample of HA was mixed with OsteoSense 750 (1:300). Solutions of 1%, 5%, 10%, and 20% of phosphoric acid (PA), sodium phosphate monobasic (M), sodium phosphate dibasic (D), and methylene phosphoric acid (MDP) were each added to each of four replicates of the HA mixed with OsteoSense 750. Three conditions were tested: incubation for 15 minutes at 37° C. after vortexing; adjusting pH to 6.5 at 23° C. after vortexing; and addition of 1% calcium chloride to each solution and incubation at room temperature after vortexing. A raw RFU value was determined for each supernatant using a fluorometer, and amount of OsteoSense 750 released was calculated as a percent of total OsteoSense 750 or total reference value. See Tables 6, 7 and 8.

Figure 19A:
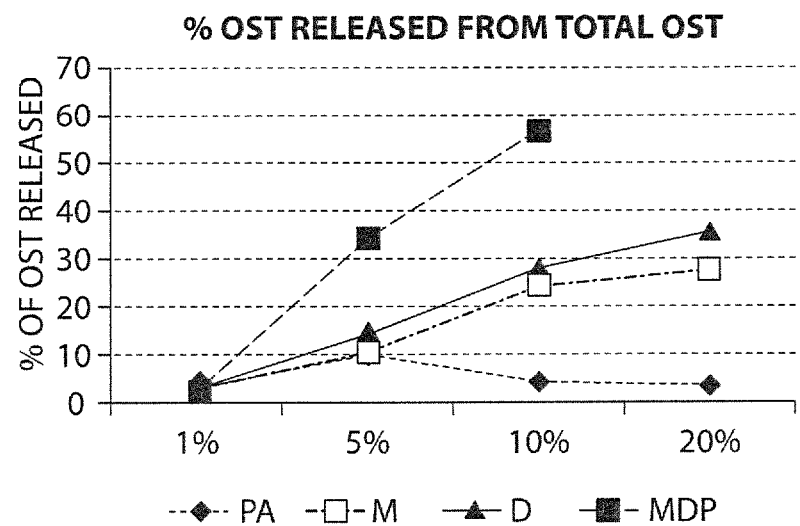
FIG. 19 is set of line graphs showing amount of OsteoSense 750 released from samples of HA powder by incubation for 15 minutes at 37° C. with each of 1%, 5%, 10%, and 20% solutions of each of phosphoric acid (PA), sodium phosphate monobasic (M), sodium phosphate dibasic (D), and methylene phosphoric acid (MDP). Graphs show relative fluorescence units (RFU) either as a percent of OsteoSense 750 released (panel A) or as a percent of total OsteoSense 750 reference value (panel B), as a function of solution concentration.
Figure 19B:
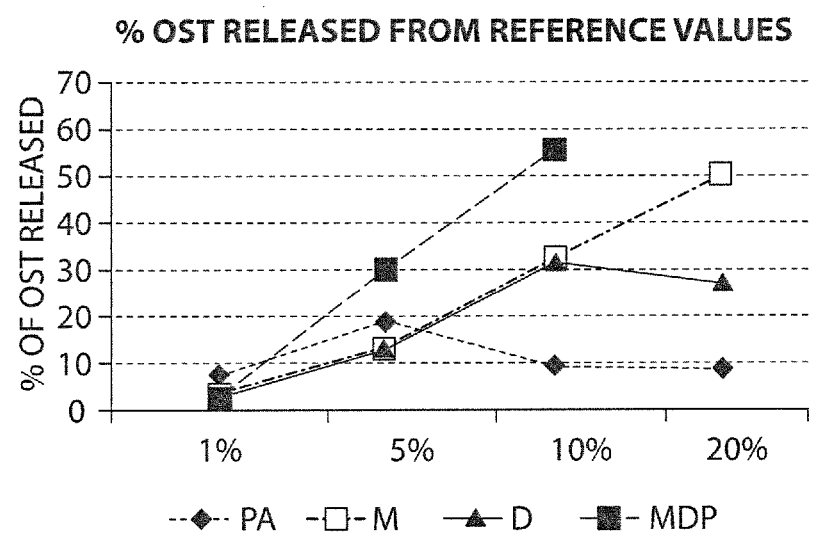
Figure 20A:
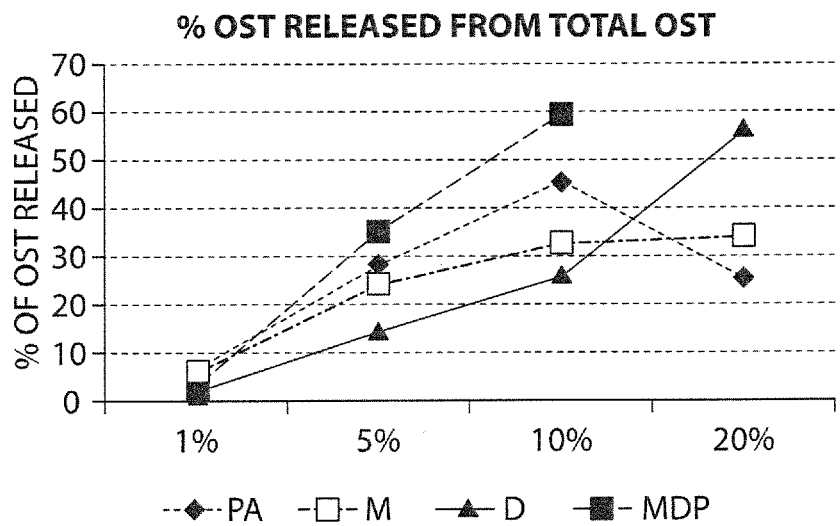
FIG. 20 is a set of line graphs showing amount of OsteoSense 750 released from HA powder by incubation at room temperature with each of 1%, 5%, 10%, and 20% solutions adjusted to pH 6.5 of each of phosphoric acid (PA), sodium phosphate monobasic (M), sodium phosphate dibasic (D), and methylene phosphoric acid (MDP). Graphs show RFU either as a percent of OsteoSense 750 released (panel A) or as a percent of total OsteoSense 750 reference value (panel B), as a function of concentration.
Figure 20B:
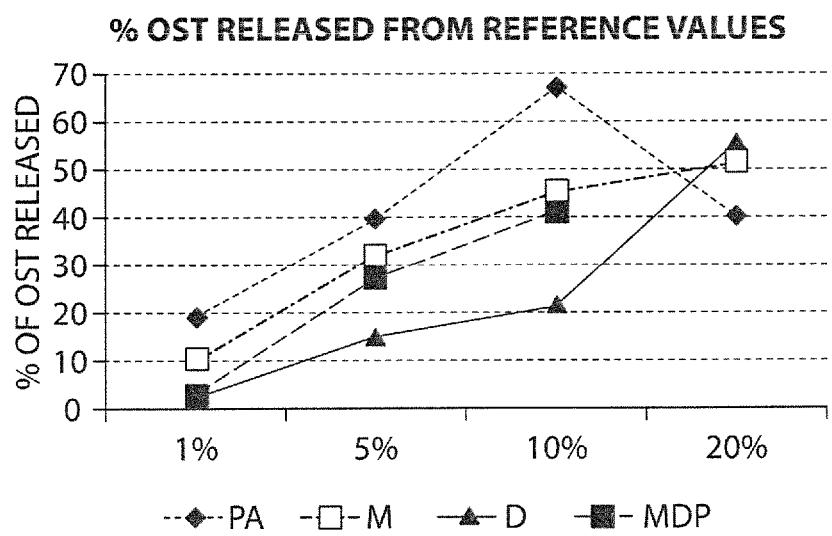
Figure 21A:
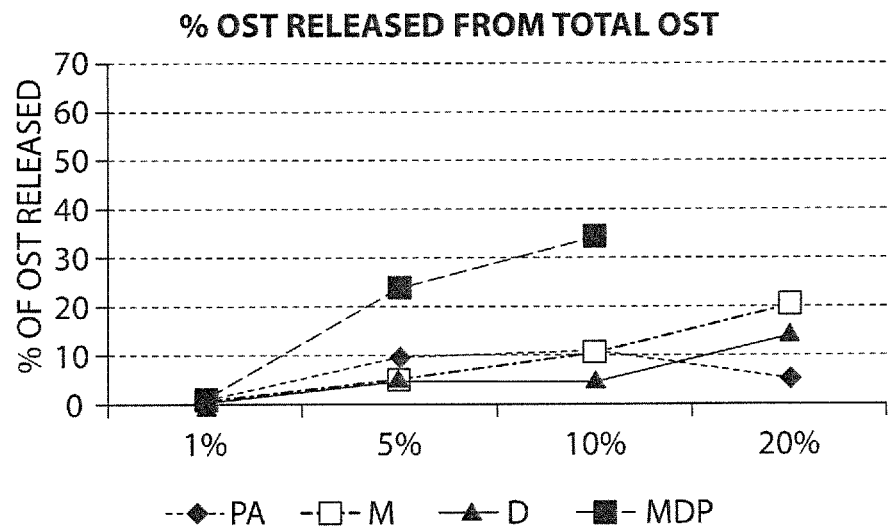
FIG. 21 is a table and line graphs showing amount of OsteoSense 750 released from HA powder by incubation at room temperature with each of 1%, 5%, 10%, and 20% solutions of each of phosphoric acid (PA), sodium phosphate monobasic (M), sodium phosphate dibasic (D), and methylene phosphoric acid (MDP), to which 1% calcium chloride was added. Graphs show RFU either as a percent of OsteoSense 750 released (panel A) or as a percent of total OsteoSense 750 reference value (panel B), as a function of concentration of solution.
Figure 21B:
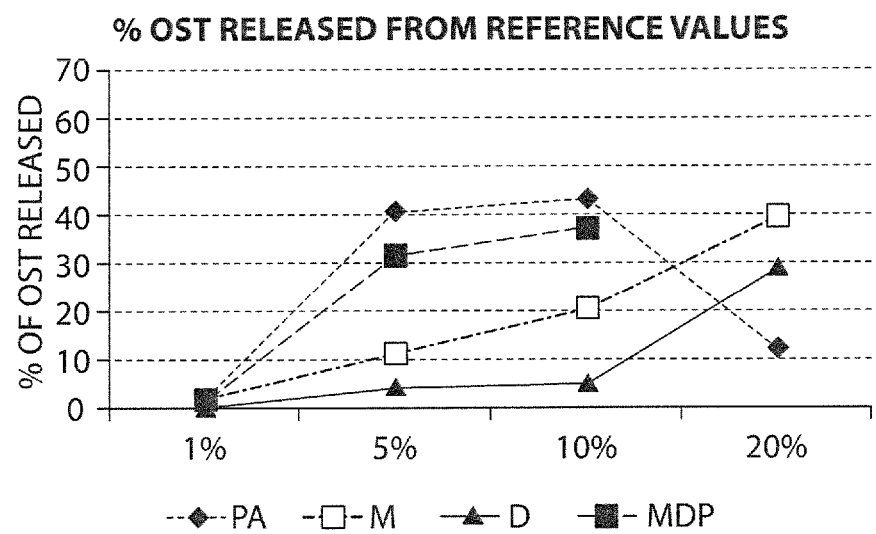

It was observed that the amount of OsteoSense 750 (Ost) released from HA was greater at higher concentrations for each of sodium phosphate monobasic, sodium phosphate dibasic, and methylene phosphoric acid solutions, which incubated for 15 minutes at 37° C. (FIG. 19). Phosphoric acid was observed to dissolve the HA. Methylene phosphoric acid was observed to remove more OsteoSense 750 from HA than sodium phosphate monobasic or sodium phosphate dibasic at each concentration (FIG. 19). At pH 6.5, methylene phosphoric acid released more OsteoSense 750 than other agents. Phosphoric acid at pH 6.5 was effective at releasing OsteoSense 750 (FIG. 20). Each of methylene phosphoric acid and phosphoric acid in calcium chloride (1%) were shown to be most effective in releasing OsteoSense 750 from HA (FIG. 21).

TABLE 6

Removal of OsteoSense 750 by incubation for 15 minutes at 37° C.

| agent (abbreviation) | | 1% solution | 5% solution | 10% solution | 20% solution |
| --- | --- | --- | --- | --- | --- |
| phosphoric acid (PA) | Raw RFU value | 1.73 | 3.67 | 1.64 | 1.33 |
| | % released of total OsteoSense | 4.61 | 9.78 | 4.37 | 3.54 |
| | % released of total reference value | 7.36 | 18.94 | 9.10 | 8.51 |
| sodium phosphate monobasic (M) | Raw RFU value | 1.16 | 3.90 | 8.97 | 10.37 |
| | % released of total OsteoSense | 3.10 | 10.41 | 23.92 | 27.67 |
| | % released of total reference value | 3.65 | 13.11 | 32.36 | 50.11 |
| sodium phosphate dibasic (D) | Raw RFU value | 1.11 | 5.33 | 10.46 | 13.30 |
| | % released of total OsteoSense | 2.97 | 14.21 | 27.90 | 35.48 |
| | % released of total reference value | 2.30 | 13.12 | 31.69 | 27.01 |
| methylene phosphoric acid (MDP) | Raw RFU value | 0.93 | 12.88 | 21.21 | −0.05 |
| | % released of total OsteoSense | 2.49 | 34.33 | 56.56 | −0.13 |
| | % released of total reference value | 2.11 | 30.09 | 55.84 | n.d. | n.d. indicates not determined

TABLE 7

Removal of OsteoSense 750 with solutions at pH 6.5, incubation at room temperature

| agent (abbreviation) | | 1% solution | 5% solution | 10% solution | 20% solution |
|---|---|---|---|---|---|
| phosphoric acid (PA) | Raw RFU value | 2.31 | 10.64 | 17.00 | 9.50 |
| | % released of total OsteoSense | 6.17 | 28.38 | 45.32 | 25.34 |
| | % released of total reference value | 18.74 | 39.54 | 67.03 | 39.91 |
| sodium phosphate monobasic (M) | Raw RFU value | 2.38 | 8.95 | 12.16 | 12.71 |
| | % released of total OsteoSense | 6.36 | 23.87 | 32.44 | 33.90 |
| | % released of total reference value | 9.73 | 31.74 | 45.17 | 51.43 |
| sodium phosphate dibasic (D) | Raw RFU value | 0.68 | 5.49 | 9.66 | 21.07 |
| | % released of total OsteoSense | 1.81 | 14.64 | 25.75 | 56.19 |
| | % released of total reference value | 2.08 | 14.63 | 21.10 | 55.57 |
| methylene phosphoric acid (MDP) | Raw RFU value | 1.35 | 13.35 | 22.41 | n.d |
| | % released of total OsteoSense | 3.59 | 35.61 | 59.77 | n.d |
| | % released of total reference value | 2.50 | 27.41 | 41.32 | n.d | n.d. indicates not determined

TABLE 8

Removal of OsteoSense 750 with calcium chloride (1%) addition to each solution, and incubation at room temperature

| agent (abbreviation) | | 1% solution | 5% solution | 10% solution | 20% solution |
|---|---|---|---|---|---|
| phosphoric acid (PA) | Raw RFU value | 0.38 | 3.54 | 3.97 | 1.92 |
| | % released of total OsteoSense | 1.01 | 9.44 | 10.57 | 5.12 |
| | % released of total reference value | 2.27 | 40.79 | 43.29 | 11.99 |
| sodium phosphate monobasic (M) | Raw RFU value | 0.22 | 2.00 | 3.85 | 7.51 |
| | % released of total OsteoSense | 0.60 | 5.34 | 10.27 | 20.04 |
| | % released of total reference value | 2.51 | 11.39 | 20.25 | 39.19 |
| sodium phosphate dibasic (D) | Raw RFU value | 0.00 | 1.75 | 1.84 | 5.26 |
| | % released of total OsteoSense | 0.01 | 4.67 | 4.90 | 14.02 |
| | % released of total reference value | 0.02 | 4.11 | 5.28 | 29.08 |
| methylene phosphoric acid (MDP) | Raw RFU value | 0.54 | 8.96 | 12.83 | n.d |
| | % released of total OsteoSense | 1.45 | 23.89 | 34.23 | n.d |
| | % released of total reference value | 1.54 | 32.07 | 37.57 | n.d | n.d. indicates not determined

The examples herein show several agents and conditions were effective for removal of OsteoSense 750 from HA. Methylene phosphoric acid was generally most effective for removing OsteoSense 750.

Example 15

Data Analysis: Sensitivity, Specificity and User Reliability

The thirty-three teeth specimens from Example 11 were analyzed by histological examination. Lesions were present in 23 of the 33 total teeth. The overall sensitivity, specificity, positive predictive value (PPV), and negative predictive value (NPV) for occlusal illumination (FO), and interproximal illumination (FI) were calculated and compared to data taken from X-rays (XR; Table 3). Standard errors were calculated using bootstrap, a nonparametric approach for evaluating the distribution of a statistic based on random re-sampling. Statistical analyses were performed using SAS version 9.1 statistical package (SAS Institute; Cary, N.C.). The user reliability, a parameter designated "inter-examiner" reliability, for each detection image obtained by occlusal illumination, interproximal illumination, and X-rays was calculated (Cohen's kappa values and Fleiss' kappa values).

Mean sensitivity, specificity, PPV, NPV and corresponding 95% confidence intervals for each of these detection methods, occlusal illumination and interproximal illumination, is shown in Table 3 in comparison to X-rays. A significant difference in sensitivity was observed between assessments and identifications using each of occlusal illumination images and X-ray images ($p<0.0001$), between assessments using each of interproximal illumination images and X-ray images ($p<0.0001$), and between assessments using each of interproximal illumination images and occlusal illumination images ($p=0.00656$). A significant difference in NPV between assessments was observed between data for the occlusal illumination images and the X-ray images ($p<0.0004$); between data for the interproximal illumination images and the X-ray images ($p<0.0001$); and between data for the interproximal illumination images and the occlusal illumination images ($p=0.031$). No statistically significant differences in specificity and PPV were observed among the occlusal illumination, the interproximal illumination and the X-ray images.

Increased inter-examiner reliability was observed using the occlusal illumination and the interproximal illumination methods compared to the conventional radiological X-ray method. A larger kappa value corresponds to an increased indication of consistency and repeatability. Cohen's kappa was calculated for each of the results using the images. The data in Table 8 show the most reliability for the occlusal illumination images compared to assessments using the other methods, based on dentists' assessments (greater kappa value) (Table 9).

TABLE 9

Inter-examiner reliability (Cohen's Kappa values) of X-rays, occlusal illumination and interproximal illumination

| method | kappa | SD |
| --- | --- | --- |
| X-ray (XR) | 0.066 | 0.264 |
| Occlusal illumination (FO) | 0.095 | 0.201 |
| Interproximal illumination (FI) | −0.105 | 0.215 |

The inter-examiner reliability from Fleiss' kappa values and 95% confidence interval was higher for assessments using the occlusal illumination images and the interproximal illumination images compared to assessments using the X-ray images (Table 10).

TABLE 10

Inter-examiner reliability (Fleiss' kappa values) of X-rays, occlusal illumination and interproximal illumination

| method | kappa | 95% CI |
| --- | --- | --- |
| X-ray (XR) | 0.284 | 0.238, 0.33 |
| Occlusal illumination (FO) | 0.768 | 0.722, 0.814 |
| Interproximal illumination (FI) | 0.66 | 0.614, 0.706 |

Occlusal illumination and interproximal illumination, the methods described herein, resulted in improved detection of dental caries compared to X-rays as shown by the statistical calculations in Tables 9 and 10. The occlusal illumination and interproximal illumination methods herein showed improved sensitivity, specificity and inter-examiner reliability.

Example 16

Statistical Analysis of Images Compared to Histological Examination

White spot lesions (WSL) were observed by histological examination in 24 of 26 teeth examined. See Example 12. The lesions in these teeth were observed to be located in a depth of less than half the enamel. These 24 teeth were assessed also using occlusal illumination and interproximal illumination images/methods described herein and compared to X-rays.

A total of 144 assessments were made by six dentists as evaluators of the 24 teeth using each of the three images/detection methods. Each assessment was categorized into a Match, an underestimation (UE) or an overestimation (OE) by comparing the result to the histological results. Histological examination data determined that all teeth had early caries, defined as lesions with a depth less than one-half enamel depth. Thus, an assessment using X-ray, occlusal illumination, and interproximal illumination images of a lesion with depth less than one-half enamel depth was categorized as a Match. Assessment of no lesion by X-rays, occlusal illumination, and interproximal illumination was categorized as an underestimation (UE) of the true lesion size by histological examination, and X-rays, occlusal illumination, and interproximal illumination assessment of Lesion with depth more than one-half enamel depth was categorized as an over estimation (OE) of the true lesion size by histological examination.

It was observed that the occlusal illumination and the interproximal illumination images/methods described herein resulted in increased detection of WSL compared to the X-ray images (Table 11). The data in Table 11 show that the dentists viewing the interproximal illumination images and the occlusal illumination images detected the highest number of WSL. Data indicate that dentists using the X-ray images scored a much higher number of incorrect No lesion assessments than the dentists using either of the methods of occlusal illumination and interproximal illumination described herein.

TABLE 11

Examiners' assessments of numbers of lesions obtained by each of X-ray, occlusal illumination and interproximal illumination methods (total for each method: 144)

| method | No lesion | Lesions less than one-half enamel depth | Lesions greater than one-half enamel depth |
| --- | --- | --- | --- |
| X-ray (XR) | 114 | 17 | 13 |
| Occlusal illumination (FO) | 77 | 42 | 25 |
| Interproximal illumination (FI) | 20 | 93 | 31 |

Statistical analyses were performed for the images/detection methods of occlusal illumination and interproximal illumination and were compared to X-rays, using a mixed-effects multinominal logistic regression model (Table 12). Statistically significant differences in odds ratio were observed for both overall misclassification compared to a Match, and for underestimated (UE) misclassification compared to a Match, for data obtained from dentists who viewed the occlusal illumination images or the interproximal illumination images compared to the X-ray images. No significant differences were observed for overestimated (OE) misclassification compared to a Match for dentists that viewed these images/methods.

The odds ratio for an overall misclassification compared to a Match for the occlusal illumination images compared to X-ray images was 0.3215, for the interproximal illumination images compared to X-ray image was 0.0708, and for the interproximal illumination images compared to occlusal illumination images was 0.2203. Data analyses show that the odds of having an overall misclassification error were 68% lower for evaluators who viewed the occlusal illumination images in contrast to those who viewed the X-ray images, and were 93% lower for evaluators who viewed the interproximal illumination images in contrast to the X-ray images. It was also observed that the odds of having an overall misclassification error were 78% lower for evaluators who viewed the interproximal illumination images compared to the occlusal illumination images.

The odds ratio for an underestimated misclassification in comparison to a Match for the occlusal illumination images compared to the X-ray images was 0.2703, for the interproximal illumination images compared to the X-ray images was 0.0309, and for the interproximal illumination images compared to the occlusal illumination images was 0.1144. Data analyses show that the odds of having an underestimated error were 73% lower for evaluators who viewed the occlusal illumination images compared to the X-ray images, and were 97% lower kr evaluators who viewed the interproximal illumination images compared to the X-ray images. The odds of having an overall misclassification error were 89% lower for evaluators viewed who the interproximal illumination images compared to those who viewed the occlusal illumination images.

These data show that the occlusal illumination images and the interproximal illumination images yield improved results compared to the conventional X-rays. Improved sensitivity in detecting caries and negative predictive values was observed using either the occlusal illumination images or the interproximal illumination images compared to the X-ray images. Improved odds ratios for both an overall misclassification and an under-estimated misclassification compared to a Match was also observed for the occlusal illumination and the interproximal illumination methods compared to X-rays. These data indicate that the methods described herein more reliably detected early stage dental caries than X-rays. Caries can be detected and therefore remineralized, without having to perform procedures that are extremely invasive, costly and painful.

TABLE 12

Odds Ratios data for comparisons of X-rays, occlusal illumination and interproximal illumination

| Odds ratios for comparing two methods | Outcome Category | | |
|---|---|---|---|
| | Overall Error and Match | UE error and Match | OE error and Match |
| occlusal illumination and X-rays | 0.3215 (p = 0.0161*) | 0.2703 (p = 0.01*) | 0.7697 (p = 0.5843) |
| interproximal illumination and X-rays | 0.0708 (p = 0.0004*) | 0.0309 (p = 0.0002*) | 0.4205 (p = 0.0975) |
| interproximal illumination and occlusal illumination | 0.2203 (p = 0.002*) | 0.1144 (p = 0.001*) | 0.5463 (p = 0.1259) |

*indicates statistical significance

What is claimed is:

1. A method for detecting an early stage dental caries in tooth enamel of a subject, the method comprising:
   contacting the enamel having the early stage dental caries with an optically detectable probe, wherein the caries is a region of demineralization in the tooth enamel, wherein the probe is a composition that selectively binds the early stage dental caries, wherein the early stage dental caries is located in a surface of the enamel at a depth selected from less than 150 micrometers; and
   detecting the caries having bound probe using an optical device that electronically detects an emission of light from the probe bound to the caries, and the early stage dental caries is detected as a gray, silver, white, brown, yellow, or translucent spot on or in the enamel surface.

2. The method according to claim 1, wherein
   the probe comprises a fluorescent probe having an excitation wavelength and an emission wavelength, wherein the fluorescent probe is selected from the group of a tetracycline, a hydrazide dye, an bisphosphonate-conjugated imaging agent, a cyanine dye, a quantum dot preparation, a tricarbocyanine dye, an near-infrared indocyanine dye, a far green two dye, a dye for fluorescence imaging, a dye that is a fluorescence agent, a macromolecule fluorescent dye, a fluorescent dye, an indocyanine green dye, a doxorubicin, a riboflavin, a chlorophyll A, a bacterial chlorophyll, and a porphyrin; and
   the method further comprises illuminating the tooth at an excitation wavelength and
   detecting the emission wavelength of the probe.

3. The method according to claim 2, wherein detecting the caries is observing an area of the emission wavelength by photometry.

4. The method according to claim 3, wherein an area having the gray, silver, white, brown, yellow, or translucent spot is an indication of a location of the caries.

5. The method according to claim 3, wherein a size of an area having the gray, silver, white, brown, yellow, or translucent spot is an indication of an extent of the caries.

6. The method according to claim 3, wherein fluorescence is detected using a device selected from the group consisting of a near-infrared (NIR) lamp, light emitting diode (LED) lamp, an ultra-violet lamp or a hand-held intra-oral device attachment connected to a detector selected from the group consisting of: a charge-coupled device (CCD) camera, an optical camera, and a spectrophotometer.

7. The method according to claim 3, further comprising detecting fluorescence by placing a separator between teeth.

8. The method according to claim 7, wherein the separator is black or gray.

9. The method according to claim 7, therein the separator reduces fluorescence from an adjacent tooth.

10. The method according to claim 2, wherein the caries with selectively bound tetracycline probe is observing a white spot.

11. The method according to claim 2, further comprising prior to contacting the enamel at least one step of: accessing an interproximal region by inserting a spacer; and delivering the probe into the interproximal area using a device selected from the group of: spray, a wedge, a tape, a metal strip, a plastic strip, a sponge, a syringe, a brush, a string, a tip, and a tray.

12. The method according to claim 11, wherein the tetracycline fluorescence probe comprises one of chlorotetracycline, oxytetracycline, and doxycycline.

13. The method according to claim 11, wherein a duration of contacting is between 10 seconds and 60 seconds.

14. The method according to claim 2, wherein the fluorescent probe is the bisphosphonate-conjugated imaging agent, and the method further comprises illuminating at an excitation wavelength of about 740 nm to about 760 nm, and diagnosing by detecting emission of fluorescence at a wavelength of about 770 nm to about 790 nm.

15. The method according to claim 2, wherein the method further comprises illuminating the tooth at the excitation wavelength is selected from the group consisting of: about 350 nm to about 450 nm for the tetracycline, about 400 nm to about 500 nm for the doxorubicin and the riboflavin, about 400 nm to about 750 nm for the quantum dot preparation, about 550 nm to about 650 nm for the porphyrin, about 600 nm to about 650 nm for the chlorophyll A, about 650 nm to about 750 nm for the bacterial chlorophyll, about 700 nm to about 770 nm for the cyanine dye, about 710 nm to about 730 nm for the fluorescent dye, about 720 nm to about 750 nm for the hydrazide dye, about 740 nm to about 760 nm for the bisphosphonate-conjugated imaging agent, the macromolecule fluorescent dye, the dye for fluorescence imaging, and the dye that is a fluorescence agent, about 750 nm to about 800 nm for the tricarbocyanine dye and the indocyanine green dye, and about 775 nm for the near-infrared indocyanine dye; and wherein detecting the emission wavelength using the optical device is selected from the group consisting of: about 450 nm to about 600 nm for the tetracycline, about 500 nm to about 700 nm for the riboflavin, about 600 nm to about 700 nm for the doxorubicin, about 650 nm to about 750 nm for the porphyrin, about 670 nm to about 900 nm for the chlorophyll A, about 750 nm to about 800 nm for the hydrazide dye, about 750 nm to about 900 nm for the quantum dot preparation, about 760 nm to about 780 nm for the fluorescent dye, about 760 nm to about 800 nm for the cyanine dye, about 770 nm to about 780 nm for the dye that is a fluorescence agent, about 770 nm to about 790 nm for the bisphosphonate-conjugated imaging agent, the macromolecule fluorescent dye, and the dye for fluorescence imaging, about 775 nm to about 825 nm for the bacterial chlorophyll, about 820 nm to about 870 nm for the tricarbocyanine dye and the indocyanine green dye, and about 845 nm for the near-infrared indocyanine dye.

16. The method according to claim 2, wherein illuminating the tooth comprises illuminating an entire tooth surface.

17. The method according to claim 16, wherein illuminating comprises scanning the surface with a beam of illuminating light.

18. The method according to claim 17, wherein the beam forms an angle relative to orientation of enamel prism.

19. The method according to 18, wherein the angle is parallel to the orientation of the enamel prism or perpendicular to the orientation of the enamel prism.

20. The method according to claim 2, wherein the illuminating the tooth comprises directing light through an occlusal layer of enamel.

21. The method according to claim 2, wherein illuminating the tooth comprises directing light to or adjacent to an interproximal area.

22. The method according to claim 2, wherein the early stage caries is located within one-half a depth of the enamel.

23. The method according to claim 1, wherein the early stage caries is prior to cavitation or advanced demineralization.

24. The method according to claim 1, wherein the caries is located in an interproximal surface between teeth.

25. The method according to claim 1, wherein the optical device is a hand-held intra-oral optical device.

26. The method according to claim 1, further comprising prior to contacting, detecting a presence of an autofluorescence.

27. The method according to claim 1, further comprising removing the probe bound to a tooth.

28. The method according to claim 27, wherein removing the probe comprises delivering a fluid with a syringe.

29. The method according to claim 28, wherein the fluid is a solution having a solute selected from the group consisting of hydrogen peroxide, phosphoric acid, sodium phosphate monobasic, sodium phosphate dibasic, methylene phosphoric acid sodium chloride, potassium chloride, pyrophosphate dibasic, and pyrophosphate tetrabasic.

30. The method according to claim 1, further comprising curing the detected caries by remineralizing.

31. The method according to claim 1, wherein the subject is a mammal.

32. The method according to claim 1, wherein the subject is a human.

33. The method according to claim 1, further comprising preparing a photographic image of an area of the caries with bound probe and comparing the image to a fluorescent image of the probe bound to caries, wherein comparing is analyzing at least one selected from the group consisting of: identity, size and depth of the caries lesion.

34. The method according to claim 1, further comprising remineralizing and monitoring the caries lesion, wherein caries development is prevented or reduced.

* * * * *